(12) United States Patent
Kravtsov

(10) Patent No.: US 6,258,553 B1
(45) Date of Patent: Jul. 10, 2001

(54) ASSAY FOR MEASURING APOPTOSIS IN CELL CULTURE

(75) Inventor: Vladimir D. Kravtsov, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/444,310

(22) Filed: Nov. 22, 1999

Related U.S. Application Data

(62) Division of application No. 08/748,885, filed on Nov. 14, 1996, now Pat. No. 6,077,684.

(51) Int. Cl.[7] ......................................................... C12Q 1/24
(52) U.S. Cl. ..................................... 435/30; 435/4; 435/32
(58) Field of Search ..................................... 435/4, 30, 32

(56) References Cited

PUBLICATIONS

Kravtsov et al. "Determination of Time–and Dose–Dependent Features of Apoptosis Induced in Human Leukemia Cells by Antitumor Drugs" *Exp. Hematol.* 24;1084, 1996.

Kravtsov, V. and Fabian, I. "Automated Monitoring of Apoptosis in Suspension Cell Cultures" *Laboratory Invest.* 74(2):557–570, Feb. 1996.

Kravstov V. and Fabian I. "Studying of Apoptosis in Human Leukemia Cells Via a Microculture Kinetic Assay" *Exp. Hematol.* 23:887, 1995.

Kravtsov et al. "A Novel Approach to Study Apoptosis in Freshly Isolated Myeloblasts and Chronic Lymphocytic Leukemia Cells" *Blood* 86(1):837a, Nov. 15, 1995.

Kravtsov et al. "A Novel Microculture Kinetic Assay (MiCK Assay) for Malignant Cell Growth and Chemosensitivity" *Eur. J. Cancer* 30A(10):1564–1570, 1994.

Li et al. "Apoptotic Cell Death During Treatment of Leukemia" *Leukemia and Lymphoma* 13(1):65–70, 1994.

Cohen, J. "Apoptosis" *Immunol. Today* 14(3):126–130, 1993.

Ross et al. "Enhancement of Daunorubicin Accumulation, Retention, and Cytotoxicity by Verapamil or Cyclosporin A in Blast Cells From Patients With Previously Untreated Acute Myeloid Leukemia" *Blood* 82(4):1288, Aug. 15, 1993.

Chiron et al. "Sensitivity of Fresh Acute Myeloid Leukemia Cells to etoposide: Relationship With Cell Growth Characteristics and DNA Single–Strand Breaks" *Blood* 80(5):1307, Sep. 1, 1992.

Holleb et al. American Cancer Society Textbook of Clinical Immunology, pp. 54–57, 1991.

*Primary Examiner*—Patrick J. Nolan
(74) *Attorney, Agent, or Firm*—Pennie & Edmonds LLP

(57) ABSTRACT

A method of measuring the apoptosis-inducing activity of a substance in cultured, isolated cells from a subject is provided, comprising: a) obtaining a sample of cells from a subject; b) isolating a single cell suspension from the sample; c) placing the cells in culture conditions; d) exposing the cells in culture to the putative apoptosis-inducing substance; e) incubating the cultured cells; f) measuring in a serial manner the optical densities of the culture to obtain an optical density curve; and g) correlating the slope of a line representing an increase over time in optical density, due to cellular membrane distortion and blebbing, with an increase in apoptotic activity. Methods of determining the anti-leukemic activity of a substance, resistance to anti-leukemic substances and the relative effectiveness of anti-leukemic agents are also provided.

9 Claims, 11 Drawing Sheets

ETHANOL time in hours

HYDROGEN PEROXIDE

A. Patient #1

B. Patient #2

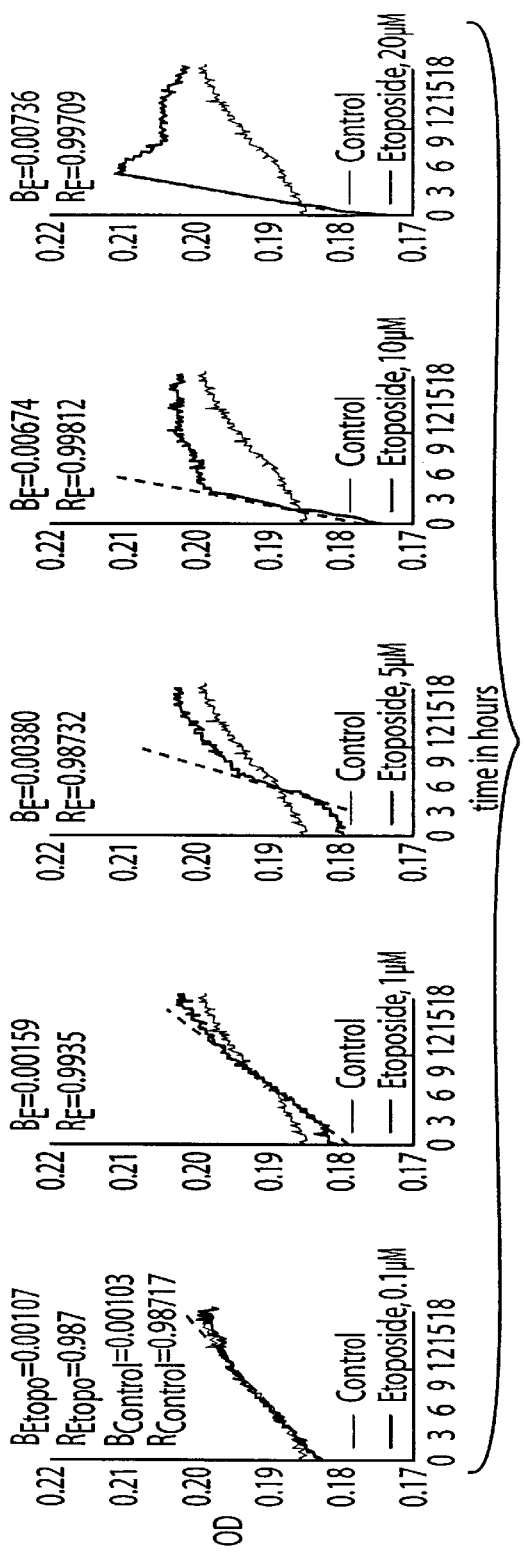
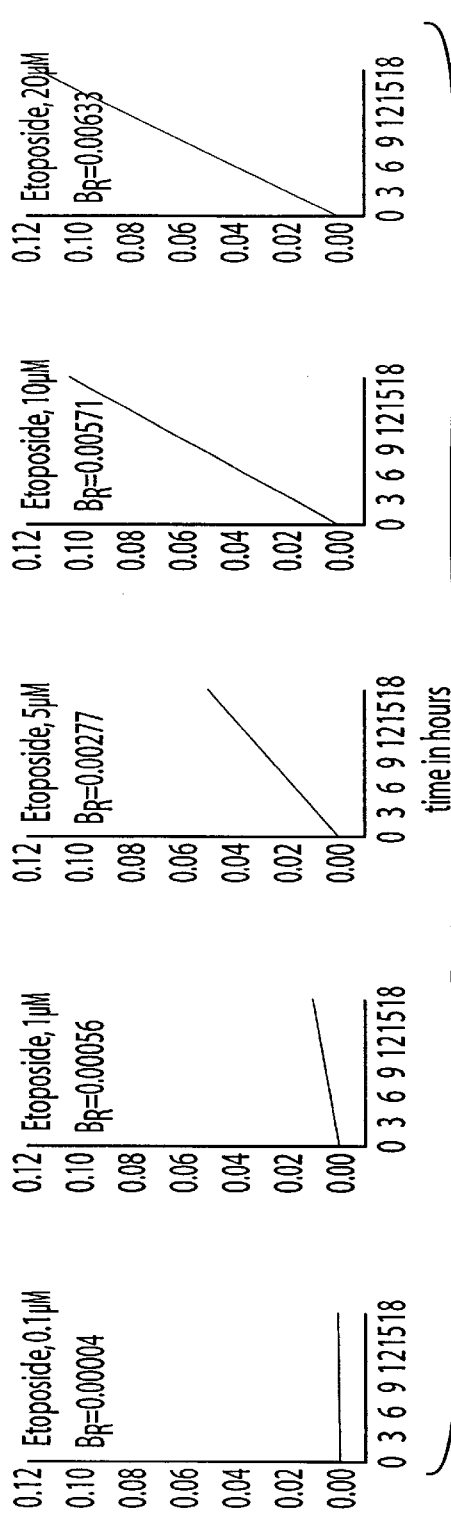
Fig. 10a
Fig. 10b

ASSAY FOR MEASURING APOPTOSIS IN CELL CULTURE

This is a division of application no. 08/748,885, filed Nov. 14, 1996 now U.S. Pat. No. 6,077,684, which is hereby incorporated by reference in its entirety.

BACKGROUND

1. Field of the Invention

The invention relates to methods of measuring apoptosis in cell culture. More specifically, the invention provides a method of measuring apoptosis in cells isolated from a subject that are exposed to a putative apoptosis-inducing substance. Even more specifically, the invention provides a method of determining the relative sensitivity and resistance of cells to a chemotherapeutic substance by measuring the apoptosis-inducing activity of the substance.

2. Background Literature

Apoptosis is distinguished from necrosis, the other well recognized form of cell death. Sudden anoxia, thermal extremes, or chemical toxicity cause necrosis. Whole areas of tissue die after these injuries and individual cells have indistinct cytological appearances and disrupted membranes. Apoptotic cells, on the other hand, are decreased in size compared to their viable counterparts due to decreased cell water and loss of membrane-bound cytoplasmic blebs[7,8]. The nuclei of apoptotic cells are homogeneously condensed and often fragmented. Internucleosomal double-stranded cleavage of nuclear DNA correlates closely with these nuclear morphological changes of apoptosis[8]. Despite nuclear fragmentation and cytoplasmic blebbing, apoptotic cells retain their energy supply for an extended period of time and their plasma membranes remain intact[7,8]. In vivo, apoptosis occurs most commonly in individual cells that are scattered among non-apoptotic, normal neighbors. Specific molecules on the surface of the apoptotic cells leads to their prompt recognition and phagocytosis by macrophages[7,8]. This rapid removal of individual cells makes apoptosis much less apparent than necrosis, in vivo. Most chemotherapeutic agents used to treat acute leukemia induce apoptosis in vitro in leukemic cells lines and freshly isolated leukemic cells[9-17]. Apoptosis has been demonstrated in the blood and bone marrow of patients receiving combined chemotherapy for acute leukemia[18]. Thus, the measurement of apoptosis in vitro should provide a means to assay for chemosensitivity of a purified leukemic cell population.

Using a population of cells, apoptosis can be identified by the cleavage of DNA at internucleosomal sites[8]. This procedure requires DNA extraction, processing, separation by size, and a means of quantifying intact and cleaved DNA. By examining individual cells within a population, the morphological appearance of apoptosis can be discerned by decreased cell size with condensed, often fragmented, nuclei[7]. A more sensitive morphological test for apoptosis is the terminal deoxynucleotidyl transferase (Tdt)-linked labeling of DNA strand ends which gives an extremely intense signal in apoptotic cells as compared to nonapoptotic ones[19]. However, these morphological methods for detecting apoptosis require cytological or histological preparations which must be examined by light microscopy, fluorescence microscopy, or fluorescence-activated cytometry. Furthermore, with each of these methods for detection of apoptosis, only one point in time may be examined per sample that is processed. Thus, it is not possible to perform real time assessments of apoptosis over time.

Chemotherapy of acute non-lymphocytic leukemia (ANLL) is successful in inducing a remission in most patients, but the majority of patients will suffer relapses and eventually succumb to their disease. These leukemias are often more resistant to chemotherapy at the time of relapse than they were at the time of initial diagnosis. This resistance to one or more chemotherapeutic agents results from the emergence of leukemic cells in the relapsed state that either incorporate less of the agent or that have developed an intracellular mechanism to circumvent the effects of the agent. Multiple factors intrinsic to the leukemia cells such as their numbers at diagnosis, specific karyotypic abnormalities[1] and the ability to grow spontaneously in culture[2,3] can be correlated with the incidence of relapse. However, these are not completely accurate predictors of relapse. The sensitivity of the leukemia to chemotherapy also appears to play a role in determining the incidence of relapses. In vitro assays of chemosensitivity have provided a means to estimate resistance to chemotherapy and thereby provide probabilities for both achieving remission and for developing relapse[4]. However, these assays are cumbersome, time consuming and not entirely reliable. Thus, a means to predict more accurately and easily at the time of initial diagnosis which patients will have a relapse is needed. It is also important to identify the chemotherapeutic agents to which an individual's relapsed leukemia has become resistant.

To achieve these aims, the invention provides a newly developed automated assay that can detect the chemosensitivity of an individual patient's leukemic cells in 48 hours or less. This assay determines the amount apoptosis or programmed cell death that a specific concentration of a chemotherapeutic agent will induce in the patient's leukemic cells.

SUMMARY OF THE INVENTION

A method of measuring the apoptosis-inducing activity of a substance in cultured, isolated cells from a subject is provided, comprising: a) obtaining a sample of cells from a subject; b) isolating a single cell suspension from the sample; c) placing the cells in culture conditions; d) exposing the cells in culture to the putative apoptosis-inducing substance; e) incubating the cultured cells; f) measuring in a serial manner the optical densities of the culture to obtain an optical density curve; and g) correlating the slope of a line representing an increase over time in optical density, due to cellular membrane distortion and blebbing, with an increase in apoptotic activity.

The invention also provides a method of determining the anti-leukemic activity of a substance, comprising: a) obtaining a sample of cells from a subject with leukemia; b) isolating a single cell suspension from the sample; c) enriching the sample for leukemic cells by removing non-leukemic cells from the sample; d) placing the enriched leukemic cells in culture; e) exposing a culture of the enriched cells to the substance; f) incubating the cultured cells; g) measuring in a serial manner the optical densities of the culture exposed to the substance; h) measuring in a serial manner the optical densities of a culture of the enriched cells not exposed to the substance; i) subtracting at each serial time point the optical densities of the culture of cells not exposed to the substance from the optical densities of the culture of cells exposed to the substance, so as to obtain the net slope (as defined above) of the serially measured optical densities due to the apoptosis-inducing activity of the . substance; and j) correlating the slope of a net.increase over time in the serially measured optical densities of the cells exposed to the substance with the anti-leukemic activity of the substance.

The invention also provides a method of determining resistance of leukemic cells to an anti-leukemic substance, comprising: a) obtaining a sample of cells from a subject with leukemia; b) isolating a single cell suspension from the sample; c) enriching the sample for leukemic cells by removing non-leukemic cells from the sample; d) placing the enriched leukemia cells in culture; e) exposing a culture of. enriched cells to the substance; f) incubating the cultured cells; g) measuring in a serial manner the optical densities of the culture of enriched cells exposed to the substance; h) measuring in a serial manner the optical densities of a culture of the enriched cells not exposed to the substance; I) subtracting at each serial time point the optical densities of the culture of cells not exposed to the substance from the optical densities of the culture of cells exposed to the substance, so as to obtain a net slope (defined as recited above) of the serially measured optical densities due to the apoptosis-inducing activity of the substance; and j) correlating the absence of a net increase or the presence of a reduced slope of a net increase over time in the optical densities of the cultures exposed to the substance with resistance to the substance.

Also provided is a method of determining the relative potential effectiveness of a substance for use in anti-leukemic therapy for a selected subject having leukemia, comprising: a) obtaining a sample of cells from the subject with leukemia; b) isolating a single cell suspension from the sample; c) enriching the sample for leukemic cells by removing non-leukemic cells from the sample; d) placing the enriched leukemic cells in culture; e) incubating the cultured cells; f) exposing a culture of the enriched cells to a first selected substance or mixture of the first selected substance and other substances; g) exposing a culture of the enriched cells to a second selected substance or mixture of the second selected substance and other substances; h) incubating the cultured cells; i) measuring in a serial manner the optical densities of the culture of enriched cells exposed to the substances or mixtures of substances; j) measuring in a serial manner the optical densities of a culture of the enriched cells not exposed to the substance; k) subtracting at each serial time point the serially measured optical densities of the culture of cells not exposed to the substance from the optical densities of the culture of cells exposed to the first substance or mixture of substances and the optical densities of the culture of cells exposed to the second substance or mixture of substances, so as to observe any differences in the net slopes in the serially measured optical densities due to differences in apoptosis-inducing activity of the first and second substances or mixtures containing the first or second substances; 1) correlating the greater slope of a net increase over time in the serially measured optical densities of the cells exposed to the first substance compared to the slope of a net increase over time in the serially measured optical densities of the cells exposed to the second substance with the greater potential effectiveness of the substance or mixture of substance in anti-leukemic therapy.

Final concentrations are shown in upper left portion of each graph. Control cultures had no additions to the medium. B is the best fit slope of the rapidly increasing segment of the experimental O.D. curves and is shown as a dashed line. R is the correlation coefficient of the best fit line. The difference between control and experimental cultures at time 0 hours is due to the 30 minute equilibration period of preincubation in the $CO_2$-controlled atmosphere prior to layering the cultures with mineral oil.

Figure 1A:
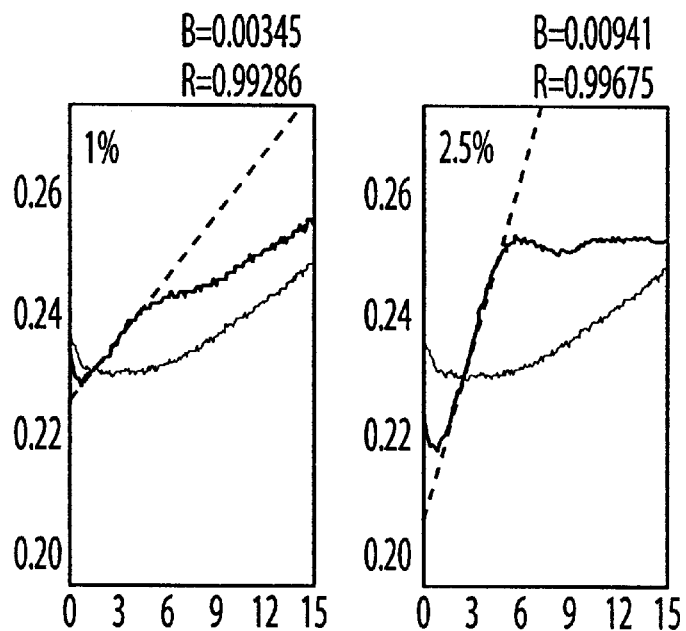
FIG. 1. Optical densities as a function of time in cultures of HL-60 cells treated with ethanol or hydrogen peroxide. Exponentially growing HL-60 cells were cultured in the MiCK assay at $1.5 \times 10^6$ cells/ml in RPMI-1640 medium (without phenol red) plus 10% heat-inactivated fetal bovine serum. O.D. readings at 600 nm of experimental cultures are shown as thick line and those of control cultures are shown as thin-line. Experimental agents added to the medium were: a) ethanol at final concentrations of 1, 2.5, 5 and 10%; b) $H_2O_2$ at final concentrations of 15, 100, 450, and 100 $\mu M$.
Figure 1A:
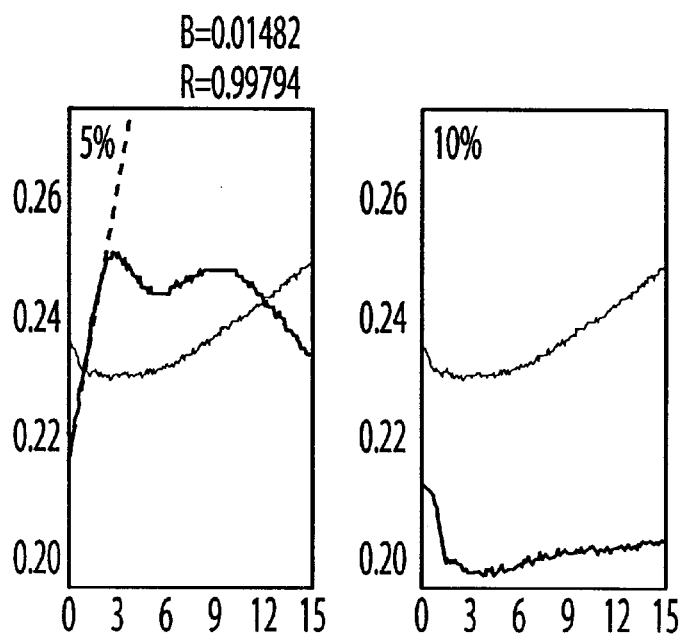
Figure 1B:
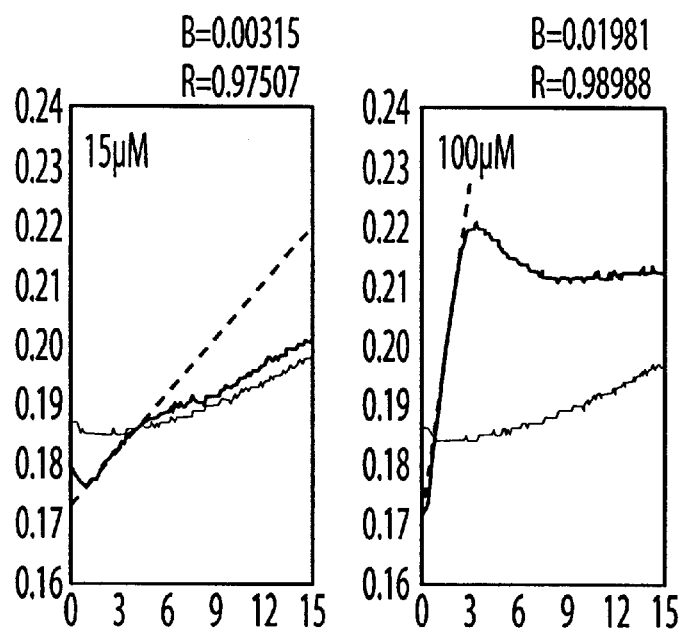
Figure 1B:
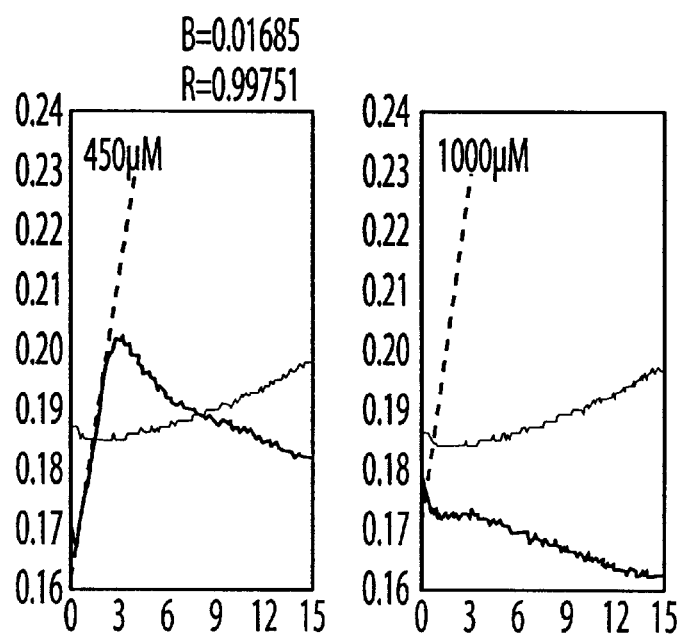
Figure 2A:
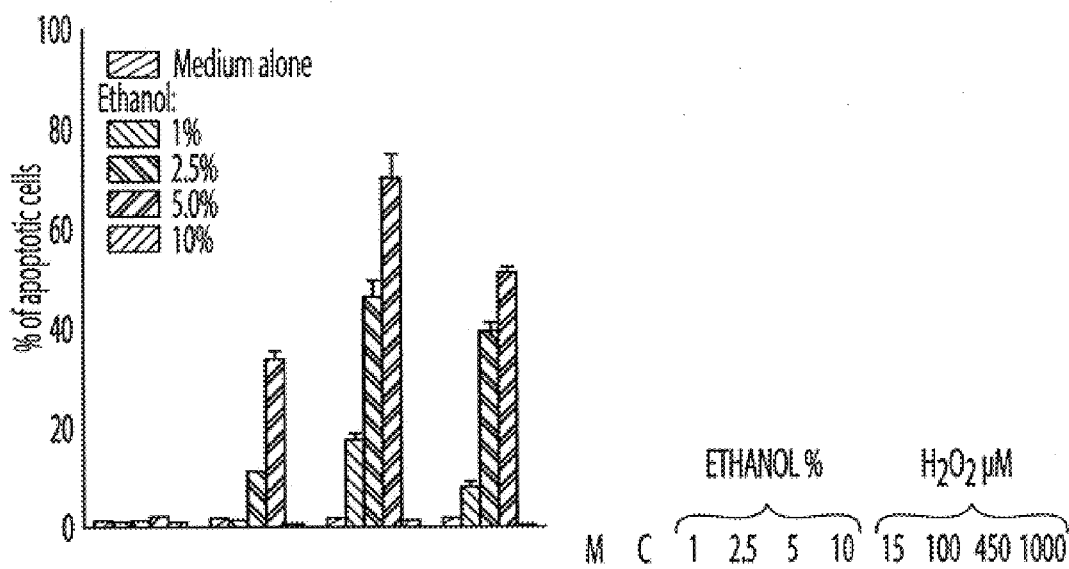
Figure 2B:
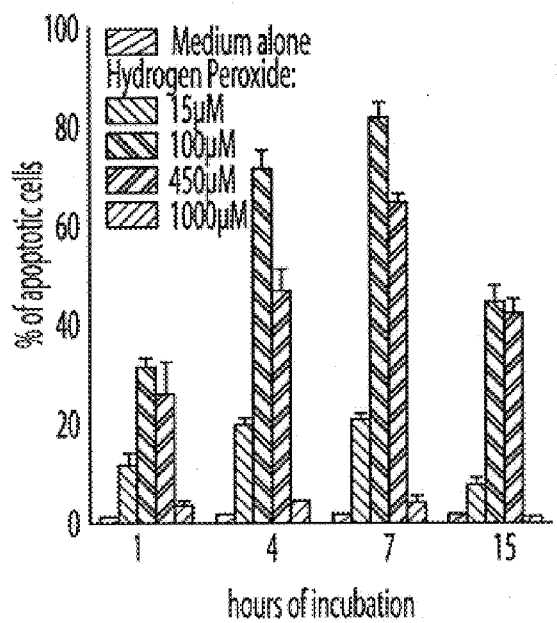

FIG. 2. Percentages of apoptotic HL-60 cells at various times during the MiCK assay. Cells from the ethanol-or $H_2O_2$-treated MiCK assays described in FIG. 1 legend were harvested at 1, 4, 7, or 15 hours. The cells were cytocentrifuged, stained with Giemsa stain, and examined microscopically for apoptotic changes of condensed and fragmented nuclei and focal protrusions of the cell surface. Treatment concentrations are indicated in the upper left. for ethanol (A) and $H_2O_2$ (B). Percentages of apoptotic cells were determined by counting 400 consecutive cells.

Figure 3:
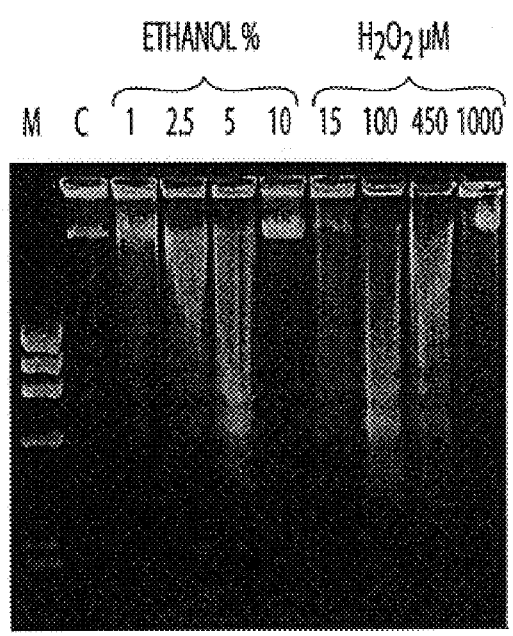

FIG. 3. Agarose gel electrophoresis of DNA from HL-60 cells after 7 hours in the MiCX assay. Cells from the ethanol-or $H_2O_2$-treated MiCK assays described in FIG. 1 legend were collected, the DNA was extracted and separated on a 1.8% agarose gel containing 0.1 $\mu g/ml$ ethidium bromide. The concentration of ethanol or $H_2O_2$ used in each assay is shown atop each lane. Lane M contains marker DNAs and lane C is DNA from cells in the control (no treatment) MiCK assay.

Figure 4A:
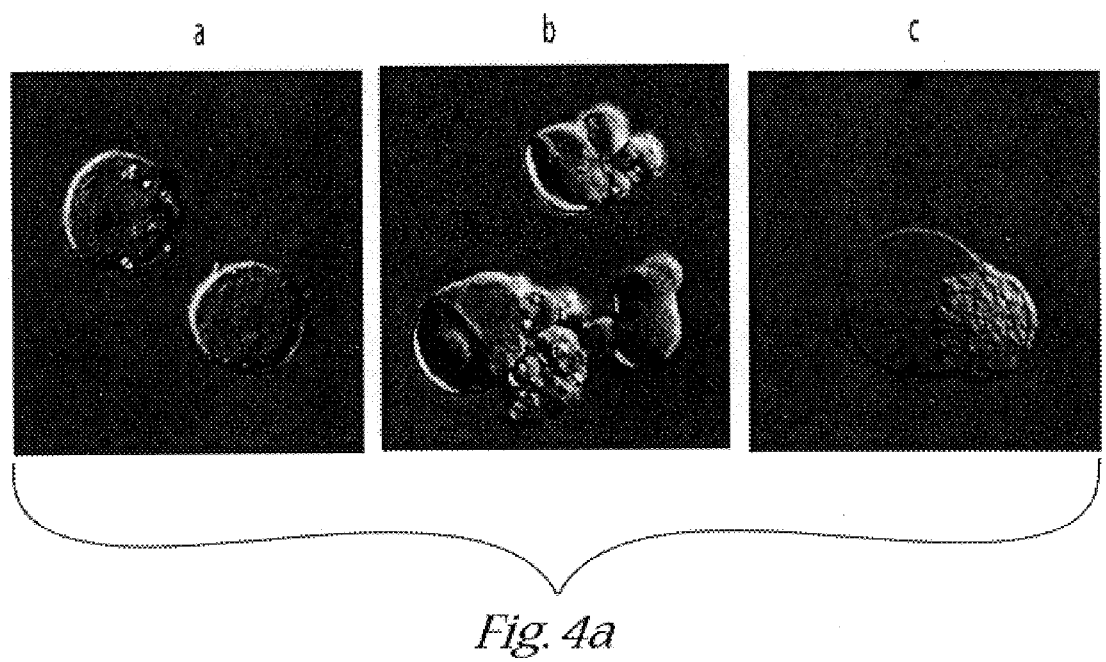
Figure 4B:
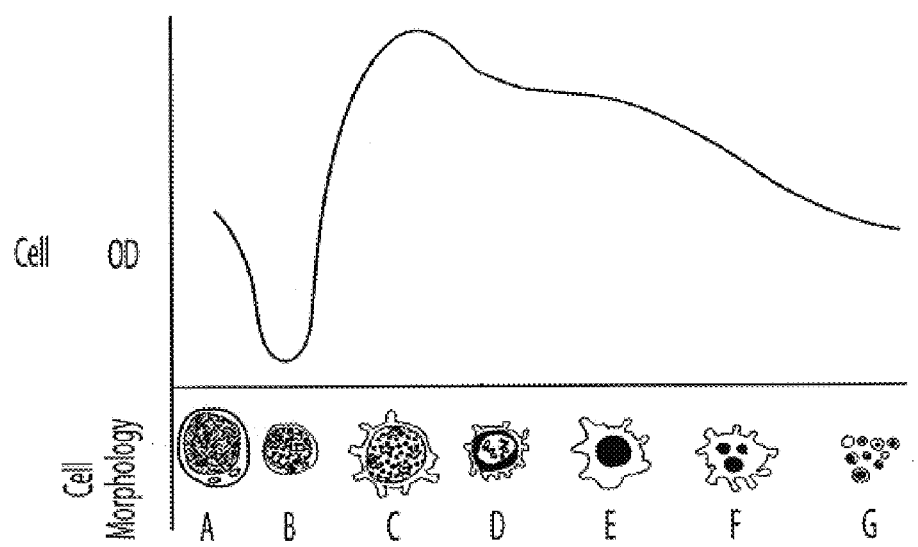

FIG. 4a. Morphological appearance of HL-60 cells with Nomarski differential interference contrast (DIC) microscopy. A. Normal untreated control cells showing large, homogeneous, central nuclei and thin rims of cytoplasm; B. Apoptotic cells after exposure to %% ethanol for 4 hours showing irregular, eccentric nuclei and prominent cytoplasmic blebbing; C. Necrotic cells exposed for 4 h to 10% ethanol showing granular eccentric nucleus and swollen cytoplasm FIG. 4b is a comparison of the typical O.D. vs. time curve seen in microcultures containing apoptotic cells with the morphological changes of those cells in the culture; (A) initial O.D. and normal morphology of cells prior to the onset of apoptosis; (B) decreasing O.D. as cells shrink due to loss of cell volume; (C) steep, rapid rise in O.D. as plasma membrane blebs; (D–G) decline in O.D. as cells disintegrate in vitro. These comparisons were made on aliquots of cells taken from parallel cultures for phase contrast and light microscopic analyses. The morphological stages of apoptosis are those defined by Cohen (Immunol Today 14:126, 1993)

Figure 5:
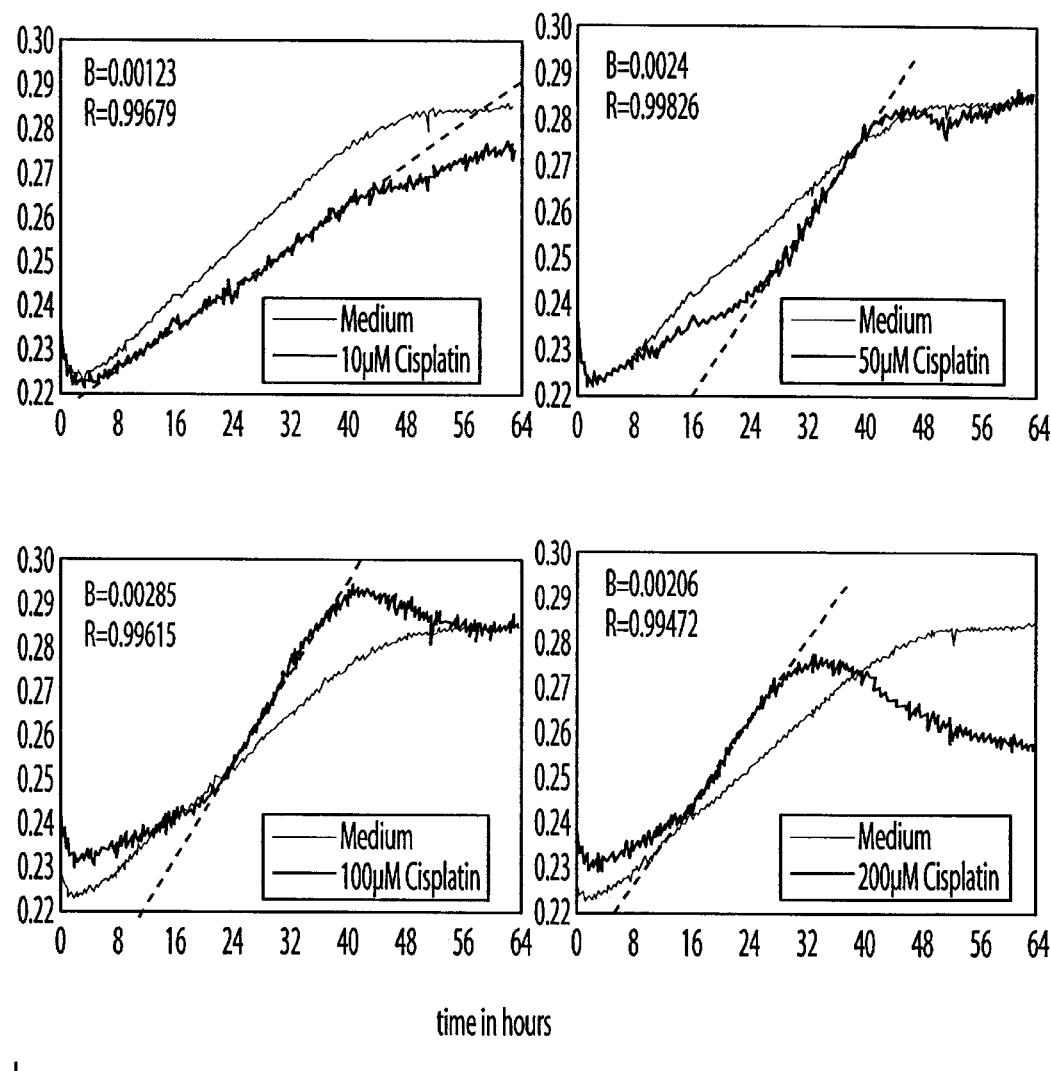

FIG. 5. Effects of varying concentrations of cis-platinum on HL-60 cells in the MiCK assay. HL-60 cells were preincubated for 4 hours in RPMI-1640 medium plus 10% fetal bovine serum containing the concentration of cis-platinum shown on each graph. Following the preincubation, the cells were washed twice in RPMI and then placed in MiCK assay. Control culture (thin line) had no cis-platinum added to the preincubations. Thick lines represent cells exposed to cis-platinum during preincubation period. B is best fit slope (graphed as dashed lines) of rapidly rising O.D. component. R is correlation coefficient of best fit line.

Figure 6A:
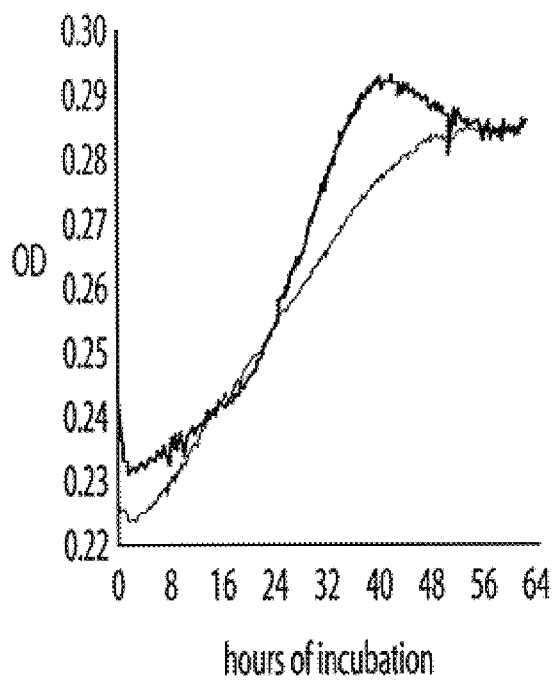
Figure 6B:
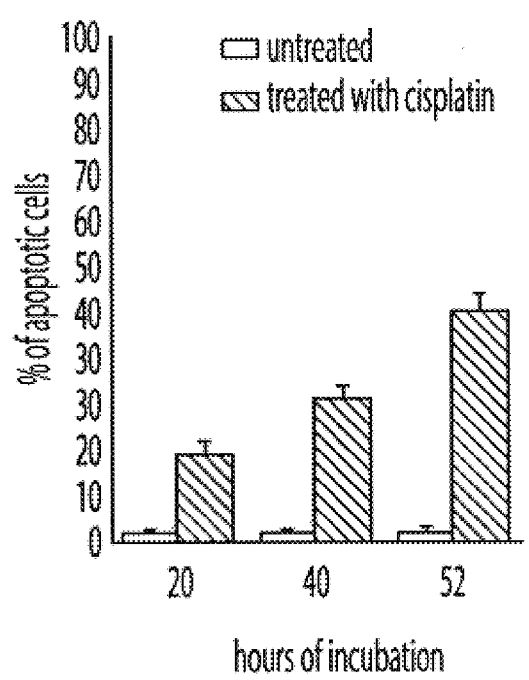
Figure 6C:
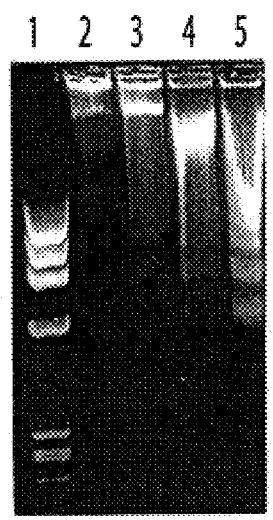

FIG. 6. Comparison of O.D. curve (A), percentage of apoptotic cells (B) and DNA cleavage (C) at various times during MiCK assay of cis-platinum-treated HL-60 cells. HL-60 cells from MiCK assays treated with 100 $\mu M$ cis-platinum as described in FIG. 5 legend were examined at 20, 40, 52 hours for percentages of apoptosis and DNA cleavage as described in legends to FIGS. 2 and 3, respectively. Lanes in DNA analysis gel are: 1-DNA markers; 2-control cells at 52 hours; 3, 4, and 5-cis platinum-treated cells at 20 h, 40 h, and 52 h, respectively.

Figure 7A:
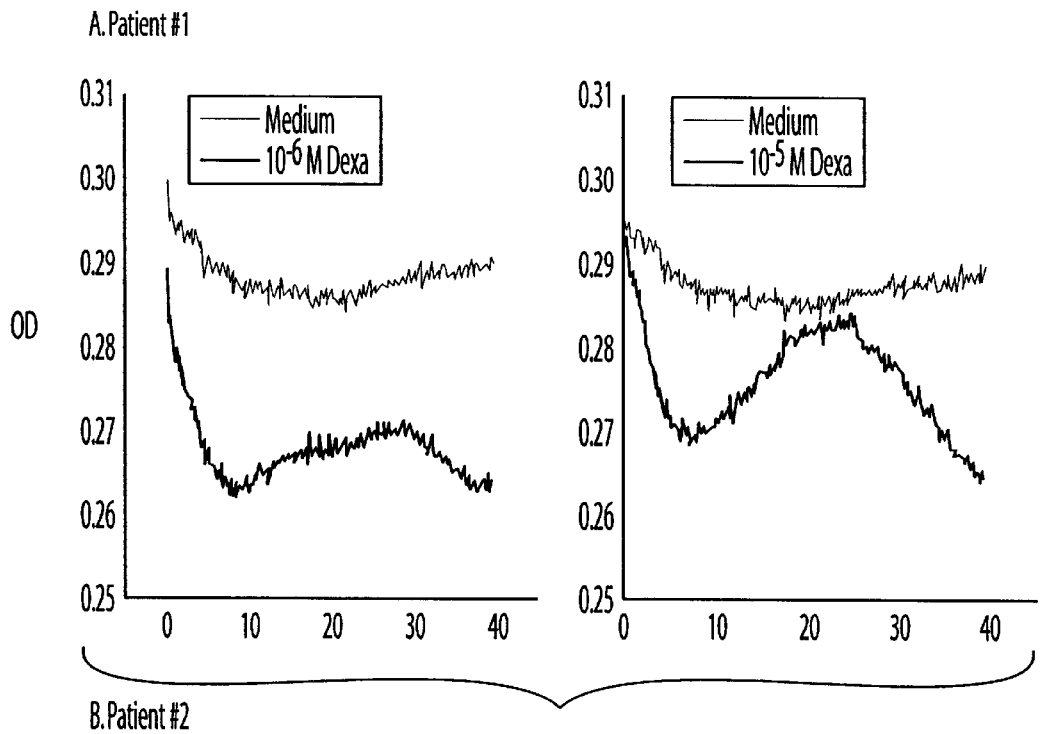
Figure 7B:
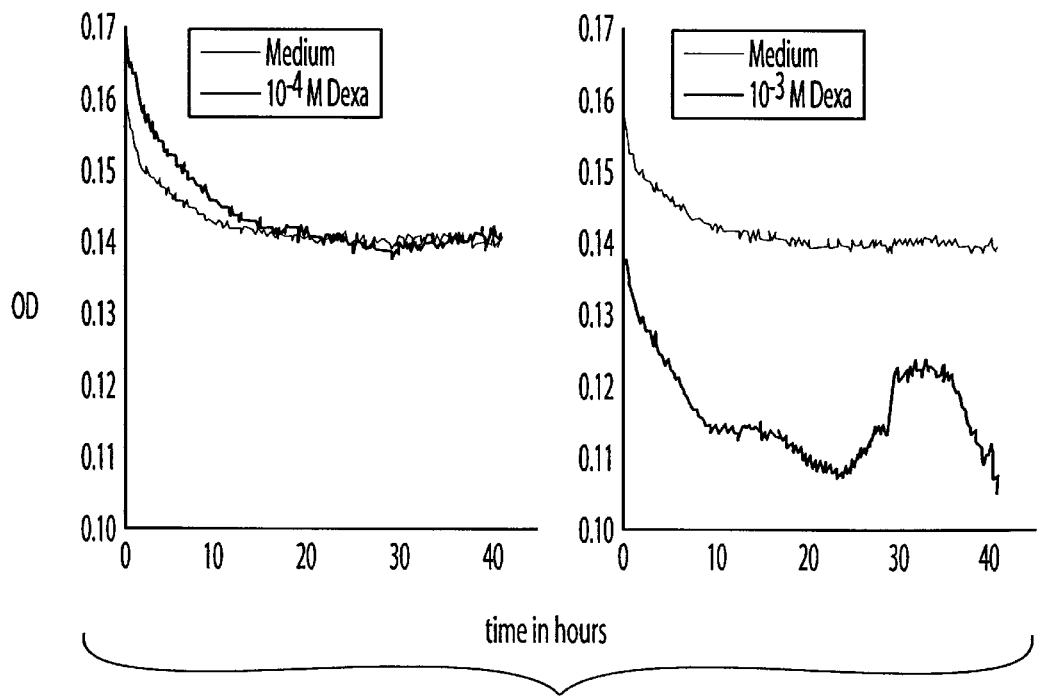

FIG. 7. O.D. changes in MiCK assay of glucocorticoid-treated human CLL cells. Peripheral blood was obtained from two different patients with B-cell CLL. Clinically, patient #1 (A) had glucocorticoid-sensitive disease while patient #2 (B) had glucocorticoid-resistant disease. A mononuclear cell fraction obtained by Ficoll-Hypaque separation was incubated for 1 h in RPMI-1640 plus 5% FCS to remove monocytes that adhered to plastic. Then T-cells were removed by sheep cell resetting and repeated Ficoll-Hypaque separation. The cells were washed and placed in the MiCK assay as described in FIG. 1 legend except that the cultures had $4 \times 10^6$ cells/ml and dexamethasone was the agent tested. Thin line is the O.D. of untreated control cells; thick line is O.D. of cells treated with concentration of dexamethasone shown on each graph.

Figure 8A:
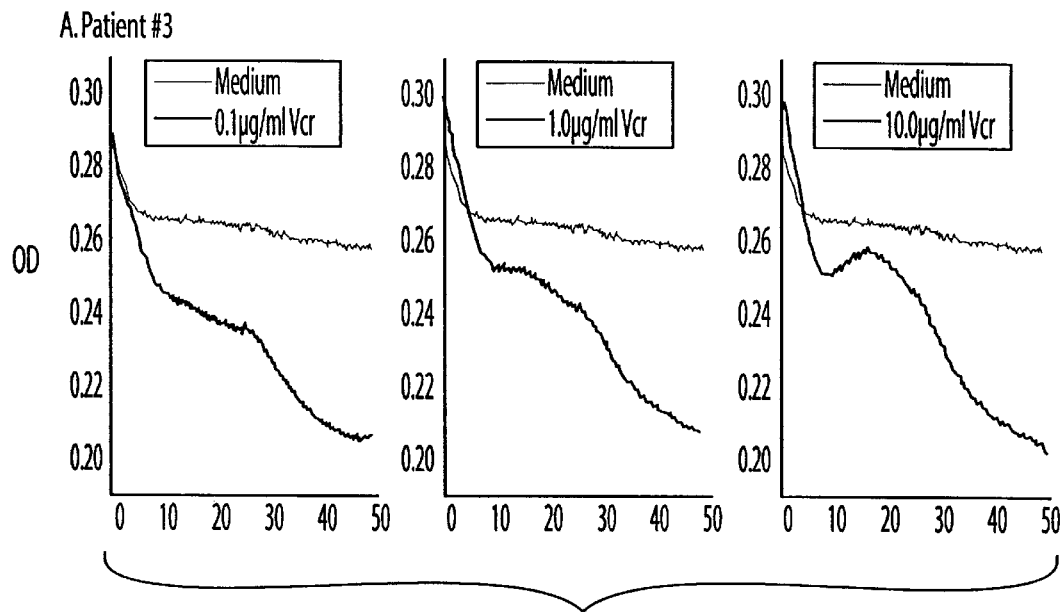
Figure 8B:
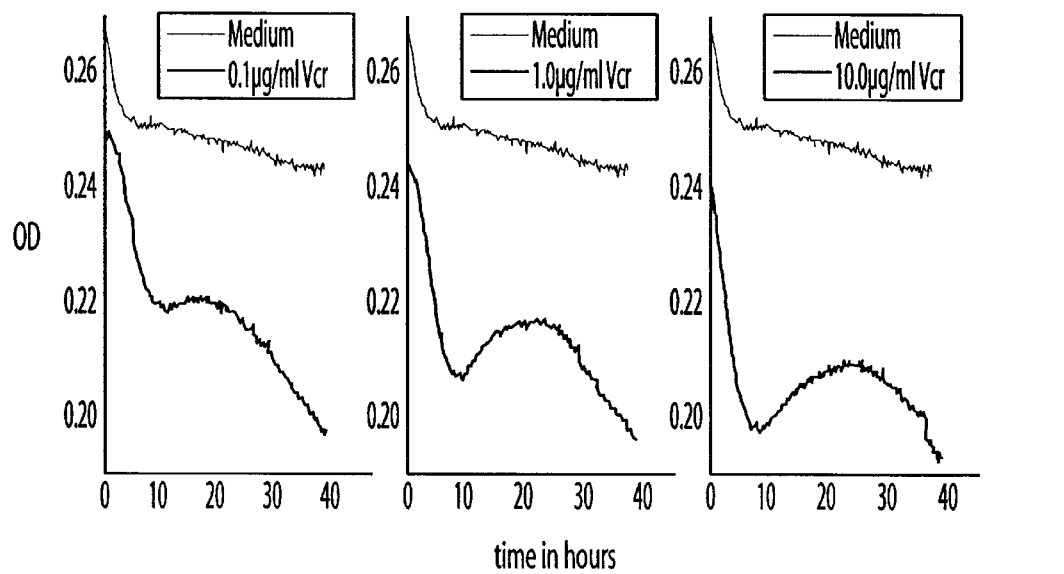

FIG. 8. O.D. changes in MiCK assay of vincristine-treated human CLL cells. The third and fourth patients with B-cell CLL had their leukemic cells purified from their blood as described in FIG. 7 legend. Clinically, patient #3 (A) had chemotherapy-resistant disease while patient #4 (B) had chemotherapy-sensitive disease. The cells were then placed in the MiCK assay with the concentrations of vincristine indicated on each graph. Thin line is O.D. of untreated control cells; thick line is O.D. of vincristine-treated cells.

Figure 9A:
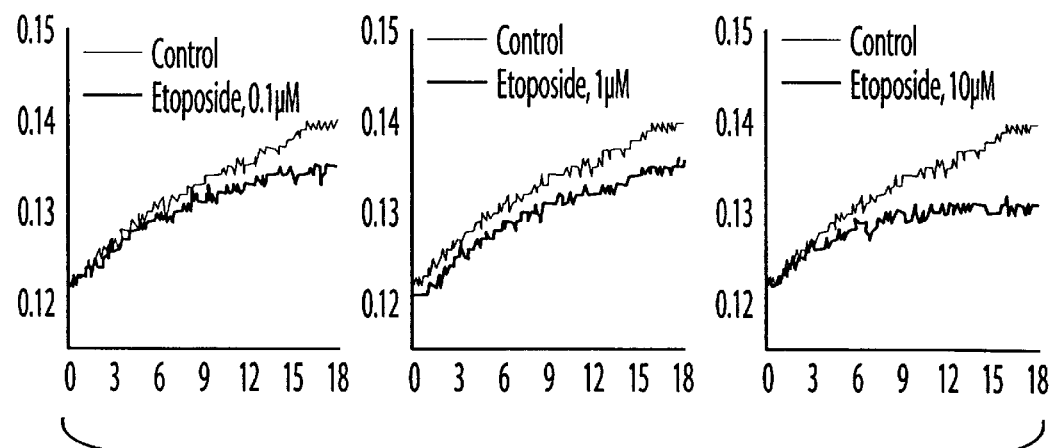
Figure 9B:
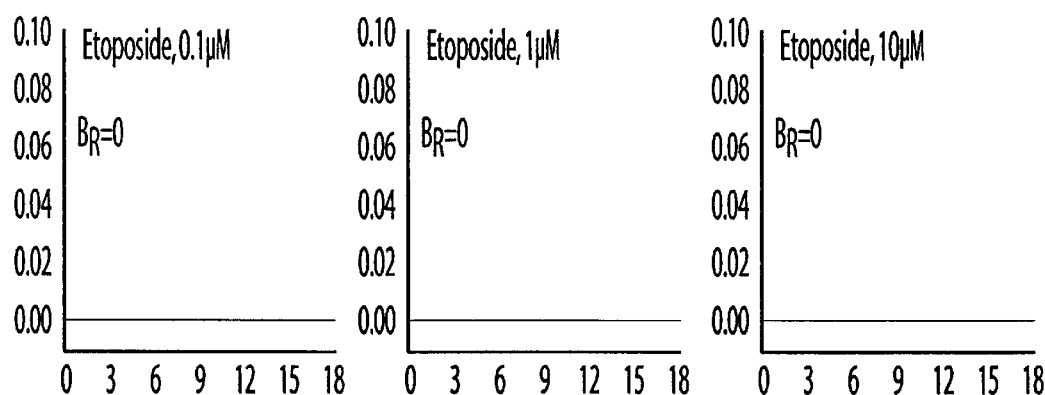

FIGS. 9A–B. Microculture kinetic assay of etoposide-treated fresh ANLL cells (Patient #1).

FIGS. 10A–B. Microculture kinetic assay of etoposide-treated fresh ANLL cells (Patient #2)

FIGS. 11A–F. Expected patterns of slopes of O.D. vs time from MiCK assays using increasing concentrations of agent with freshly isolated ANLL cells. These slopes will be calculated by subtracting the slope of untreated, control ANLL cells from the slope of the same ANLL cells when they are exposed to a dose of a chemotherapeutic agent. See FIGS. 9 & 10 (p. 27) and description of these figures (p. 10) for examples of pattern F (FIG. 9) in a chemotherapy resistant leukemia and pattern B (FIG. 10) in a chemotherapy sensitive leukemia.

DETAILED DESCRIPTION OF THE INVENTION

A method of measuring the apoptosis-inducing activity of a substance in cultured, isolated cells from a subject is provided, comprising: a) obtaining a sample of cells from a subject; b) isolating a single cell suspension from the sample; c) placing the cells in culture conditions; d) exposing the cells in culture to the putative apoptosis-inducing substance; e) incubating the cultured cells; f) measuring in a serial manner the optical densities of the culture to obtain an optical density curve; and g) correlating the slope of a line representing an increase over time in optical density, due to cellular membrane distortion and blebbing, with an increase in apoptotic activity.

The key step in the present methods is the step of correlating the slope of a line representing the optical density of the culture with the presence, absence, increase or decrease of apoptosis-inducing activity in the culture. An increase in the net slope of optical density measurements is shown in the present invention to be correlated with an increase in apoptotic activity. This increase in the slope of the optical density curve is shown by the present data analysis to be due to the cellular membrane distortion and blebbing that occurs during apoptosis. Furthermore, as recited in the embodiments of the present method described below, the invention also teaches the correlation of an increase in the slope of the optical density curve of a culture of a patient's cells with a specific clinical outcome for that patient. Thus, the invention provides a rapid and simple method for assessing patient prognoses and for selecting chemotherapeutic drugs and dosages tailored to the particular patient.

By "net slope" is meant the slope of an experimental culture after subtraction of the slope of a relevant control culture. The net slope can be calculated either by subtracting the optical density measurements of the control group from the experimental group at each serial time point or by calculating the slope of the control curve and subtracting it from the calculated slope of the experimental curve.

The present methods can be applied to test any putative chemotherapeutic agent for apoptosis-inducing activity. The present methods can be applied to assays for any disease that would be treated by reducing a population of cells, that is, where apoptosis is desired. Such diseases include malignancies (further describe below), diseases characterized by overgrowth of a population of cells (e.g., Cushing's syndrome, psoriasis, etc.), autoimmune diseases (e.g., lupus, Crohn's disease, rheumatoid arthritis, etc.) among others.

The present methods can be applied to test any putative chemotherapeutic agent for apoptosis-inhibiting activity. "Substance" as used herein includes chemicals as well as viral agents. The present methods can be applied to assays for diseases caused by or associated with spontaneous apoptosis. Such diseases include aplastic anemias or red cell aplasias caused by viral infections (e.g., parvovirus) and HIV disease among others.

The step of obtaining cells from a subject (e.g., a patient) is not limited to a particular source or means of obtaining or isolating cells. The cells can be primary cells isolated directly from tissue sample obtained from a subject. As used herein "tissue sample" includes blood, bone marrow, tumors, and body fluids (e.g., pleural fluid, peritoneal fluid, cerebrospinal fluid). Alternatively, the cells obtained can be from a sustained culture of cells obtained from a patient and maintained in culture for a finite period of time. In a further alternative, the cells can be obtained from an immortalized culture of cells derived from cells isolated from a subject (e.g., HL-60, CEM leukemia cell line).

A single cell suspension requires that cells from a solid tissue be separated from each other and maintained separated from each other. Thus, the culture conditions of the present methods are those which substantially avoid or reduce the adherence of the cultured cells to the culture container (e.g. culture well, multiple well plate, multiple well microplate, etc.) and the other cells in the suspension. With blood cells, active steps are not usually required to avoid adherence. However, the presence of a low percentage of cells which adhere to each other or the culture container do not negate the effectiveness of the method. Up to 10% of the cells can be adherent without negatively impacting the effectiveness of the method. An example of culture conditions is provided below in the examples.

The concentration of cells in the single cell suspension is preferably from about $1.0 \times 10^5$ to about $4.0 \times 10^5$ cells per 250 microliters. For solid tumors of non-lymphoid or non-hematopoietic origin, a significantly lower concentration of cells (e.g., as low as $1.0 \times 10^4$) would be sufficient. Furthermore, as the microplates and microplate readers used in these methods improve, even lower concentrations (e.g., as low as $1.0 \times 10^3$) will be sufficient.

The step of exposing the cultured cells to a substance and/or agent can be by simply adding the substance and/or agent to a culture container having the single cell suspension therein. Alternatively, the cells can be transiently exposed to the substance, which would be washed off the cells prior to beginning the incubation and measuring steps.

In certain embodiments of the method (e.g., for making assessments of likely patient relapse due to, for example, initial resistance or acquired resistance), the substance referred to can be a known apoptosis-inducing agent or a known chemotherapeutic agent (e.g., an anti-leukemic agent). Examples of these substances include idarubicin, mitoxantrone, daunorubicin, etoposide, cytosine arabinoside, vinblastine, vincristine, doxorubicin, fludarabine, cis-platinum, cladribine and dexamethasone. Alternatively, in an embodiment of the method for identifying agents that have chemotherapeutic or apoptosis-inducing activity, substances not previously associated with apoptosis-inducing activity or chemotherapeutic activity are used in the method.

The step of incubating the cultured cells requires maintaining the cells in culture conditions in the presence of the substance and/or agent (or after transient exposure to the substance). A step of preincubating the cells at about 37° C. in water-saturated air (or approximately 100% humidity) containing about 5% carbon dioxide assists in maintaining the appropriate pH and state of hydration of the culture during incubation and reading. In one embodiment, the humidity and pH are maintained by incubation in the sealed well of a 96 well microplate in an incubated spectrophotometer. For example, mineral oil can be overlaid atop the cells, thus hermetically sealing the culture container. The method can further comprise the step of preventing gas bubbles from forming in the cell culture during incubation. This can be accomplished by using any appropriate microwell plate. A preferred example is the "one half well" microplates by Corning (catalog #43027).

The step of measuring the optical density of the culture is done by measuring absorbance at about 550 to 650 nanometers. The optical densities of the cultures are preferably read after shaking. In a preferred method, the step of measuring optical densities takes place in a microwell plate in an incubated microwell plate reader. Although all microplates are expected to work, the "one half well" microplates described above are preferred. These microwell plates have a shape that allows for the use of fewer cells and they are treated for tissue culture. Other plates with similar features can also be used.

The serial manner in which the optical densities are measured is merely what is required to able to plot a slope for the optical densities of the culture of cells. Thus, measurements must be taken over time. The time point for and frequency of each serial measurement of a culture can be chosen based on the cells being cultured and the expected time course of apoptosis induction by a substance known to have apoptotic activity.

The invention also provides a method of determining the anti-leukemic activity of a substance, comprising: a) obtaining a sample of cells from a subject with leukemia; b) isolating a single cell suspension from the sample; c) enriching the sample for leukemic cells by removing non-leukemic cells from the sample; d) placing the enriched leukemic cells in culture; e) exposing a culture of the enriched cells to the substance; f) incubating the cultured cells; g) measuring in a serial manner the optical densities of the culture exposed to the substance; h) measuring in a serial manner the optical densities of a culture of the enriched cells not exposed to the substance; i) subtracting at each serial time point the optical densities of the culture of cells not exposed to the substance from the optical densities of the culture of cells exposed to the substance, so as to obtain the net slope (as defined above) of the serially measured optical densities due to the apoptosis-inducing activity of the substance; and J) correlating the slope of a net increase over time in the serially measured optical densities of the cells exposed to the substance with the anti-leukemic activity of the substance.

The key step in the present method is the step of correlating the slope of a line representing an increase in the optical density of the culture with the anti-leukemic activity of a substance. An increase in the net slope of optical density measurements is shown in the present invention to be correlated with an increase in anti-leukemic activity. The invention teaches the correlation of an increase in the slope of the optical density curve of a culture of a leukemic patient's cells with a specific clinical outcome for that patient. Thus, the invention provides a rapid and simple method for assessing the prognosis of a leukemic patient and for selecting anti-leukemic drugs and dosages tailored to the particular patient.

This method can be used not only to select an appropriate chemotherapeutic for leukemia, but can also be used to select appropriate doses of the anti-leukemic agent. In the determination of appropriate doses, the method is carried out in the same manner, but with multiple experimental cultures exposed to the same substance at different doses. Because of the automated nature of the method, it is reasonable to test several substances at several concentrations each at the same time for their effectiveness as a chemotherapeutic agent. As recited in a further embodiment of the method described below, the method can also be used to compare and determine the relative effectiveness of several substances, because the steepness of the slope is correlated with the relative effectiveness.

For each step in the present method that is the same step as recited in the previously described method, the definition of terms and description of preferences applies to the present method, unless otherwise specified.

For assays relating to leukemia, the tissue sample is blood, bone marrow, pleural fluid, cerebrospinal fluid or peritoneal fluid, and the enriching step removes at least 98.0% of erythrocytes and at least 90% of normal nucleate blood cells (e.g., lymphocytes, monocytes and granulocytes). An example of the specific steps used to enrich a suspension of cells is described in detail in the Examples.

The invention also provides a method of determining resistance of leukemic cells to an anti-leukemic substance, comprising: a) obtaining a sample of cells from a subject with leukemia; b) isolating a single cell suspension from the sample; c) enriching the sample for leukemic cells by removing non-leukemic cells from the sample; d) placing the enriched leukemia cells in culture; e) exposing a culture of enriched cells to the substance; f) incubating the cultured cells; g) measuring in a serial manner the optical densities of the culture of enriched cells exposed to the substance; h) measuring in a serial manner the optical densities of a culture of the enriched cells not exposed to the substance; I) subtracting at each serial time point the optical densities of the culture of cells not exposed to the substance from the optical densities of the culture of cells exposed to the substance, so as to obtain a net slope (defined as recited above) of the serially measured optical densities due to the apoptosis-inducing activity of the substance; and j) correlating the absence of a net increase or the presence of a reduced slope of a net increase over time in the optical densities of the cultures exposed to the substance with resistance to the substance.

The key step in the present method is the step of correlating the slope of a line representing a reduced net increase in the optical density of the culture over time with the resistance of a subjects cells to a substance. The invention teaches the correlation of an decrease in the slope of the optical density curve of a culture of a leukemic patient's cells with a specific clinical outcome for that patient, particularly, the resistance of that patient to a given chemotherapeutic agent. By teaching this correlation, the method can also be used to predict likelihood of relapse of a patient at the time of diagnosis if treated with the substance for which resistance is shown. Thus, the invention provides a rapid and simple method for assessing the prognosis of a leukemic patient and for selecting anti-leukemic drugs and dosages tailored to the particular patient.

This method can detect a reduction in the current apoptotic response of a subject compared to the response of the same subject with the same substance in the past. Preferably, this comparison will be based on the same dose over the same time course as previously measured. It is also possible to compare an old and new sample from the same subject. Alternatively, the comparison can be with the response of a standardized cell line previously shown to respond to the substance. The comparison can also be with cells from an untreated patient (not the subject) previously shown to respond to the substance. In these methods one looks at the net slope to see if the slope is flat (equal to zero) or flatter than the reference slope (e.g., the previously obtained slope for this patient with this drug).

For each step in the present method that is the same step as recited in a previously described method, the definition of terms and description of preferences applies to the present method, unless otherwise specified.

Also provided is a method of determining the relative potential effectiveness of a substance for use in antileukemic therapy for a selected subject having leukemia, comprising: a) obtaining a sample of cells from the subject with leukemia; b) isolating a single cell suspension from the sample; c) enriching the sample for leukemic cells by removing non-leukemic cells from the sample; d) placing the enriched leukemic cells in culture; e) incubating the cultured cells; f) exposing a culture of the enriched cells to a first selected substance or mixture of the first selected substance and other substances; g) exposing a culture of the enriched cells to a second selected substance or mixture of the second selected substance and other substances; h)incubating the cultured cells; i) measuring in a serial manner the optical densities of the culture of enriched cells exposed to the substances or mixtures of substances; j) measuring in a serial manner the optical densities of a culture of the enriched cells not exposed to the substance; k) subtracting at each serial time point the serially measured optical densities of the culture of cells not exposed to the substance from the optical densities of the culture of cells exposed to the first substance or mixture of substances and the optical densities of the culture of cells exposed to the second substance or mixture of substances, so as to observe any differences in the net slopes in the serially measured optical densities due to differences in apoptosis-inducing activity of the first and second substances or mixtures containing the first or second substances; 1) correlating the greater slope of a net increase over time in the serially measured optical densities of the cells exposed to the first substance compared to the slope of a net increase over time in the serially measured optical densities of the cells exposed to the second substance with the greater potential effectiveness of the substance or mixture of substance in antileukemic therapy.

The key step in the present method is step of correlating a relatively greater slope of optical densities for a culture exposed to one substance compared to the slope of optical densities for a culture exposed to a different substance with a higher level of effectiveness as a chemotherapeutic agent. The term "potential effectiveness" means the likelihood of sustained remission. It can alternatively mean sustained remission with a low level of toxicity. Relative potential effectiveness merely signifies a comparison of the likelihood of remission with different substances or different doses or different mixtures of a substance and other substances or agents. Thus, the relative suitability or appropriateness or a given treatment regimen can be determined according to this method.

For each step in the present method that is the same step as recited in a previously described method, the definition of terms and description of preferences applies to the present method, unless otherwise specified.

The mixtures referenced in the present method can be a combination of a first and a second substance compared to just the first or the second substance alone. The mixture can be of a first or second substance and one or more other substances (e.g., additional chemotherapeutics or agents that enhance the activity of chemotherapeutics)

The present methods can be applied to all types of leukemias, including acute and chronic myeloid (non-lymphocytic or non-lymphoblastic) leukemia, as well as acute and chronic lymphocytic leukemia. The above methods can be applied to non-Hodgkins lymphoma when there are sufficient populations of malignant cells to be isolated. For these diseases, the methods are essentially as describe above.

The present methods can be applied to malignancies other than leukemia, for example, any malignancy from which a single cell suspension can be obtained and cultured under conditions which significantly avoid the adherence of the cells to the culture well and the other cells in the suspension. For example, any type of solid tumor, including, but not limited to lymphoma, breast cancer, colon cancer, lung cancer, prostate cancer and melanoma can be used as the single. cell suspension of the methods. Tissue samples containing these cells can be the tumor itself or pleural, peritoneal or cerebrospinal fluids which can contain cancerous cells. In the case of solid tumors the enrichment step would not generally be used. Otherwise the methods are essentially as describe above.

In the above methods the substance can be any chemotherapeutic agent. For example, the substance can be selected from the group consisting of idarubicin, mitoxantrone, daunorubicin, etoposide, cytosine arabinoside, vinblastine, vincristine, doxorubicin, fludarabine, cis-platinum, cladribine and dexamethasone.

The above methods can further comprise the step of additionally exposing the culture of cells to an agent that affects the intracellular concentration of the substance. This agent can be any modulator of drug sensitivity, including growth factors and antibodies to leukemic cells. Currently available examples include cyclosporine A and verapamil among others.

EXAMPLES

Assay of Apoptosis in Assessing the Chemosensitivity of Leukemias

The present assay of apoptosis is used to assess the chemosensitivities of purified leukemia cells obtained from patients at the time of initial diagnosis of acute leukemia. The present assay results for each patient are correlated with a) the clinical response of that patient to chemotherapy in terms of achieving remission and developing relapse and b) other prognostic factors such as leukemic cell counts, cytogenetic abnormalities, and immunophenotype.

Identifying Resistance to Specific Chemotherapeutic Agents in Relapsed Leukemia.

In each patient that achieves a remission and then relapses, the present assay of apoptosis is used to compare the chemosensitivities of the patient's leukemic cells after relapse with the results obtained at the time of initial diagnosis. In those patients whose leukemic cells have developed a specific chemoresistance, comparison is made of leukemia cells from initial diagnosis and from relapse for known causes of chemoresistance such as increased bcl-2 or mdr-1 gene expressions or expression of a mutated p53 gene.

SUMMARY AND ADVANTAGES

The present assay detects quantitative changes in leukemic cells throughout a period of apoptosis that is induced by a chemotherapeutic agent. This assay is useful in analyzing the sensitivities of an individual patient's leukemic cells to a variety of chemotherapeutic agents.

Previous chemosensitivity assays for acute leukemia have been based upon either clonal colony growth of the leukemic cells with pulse or continuous exposures to chemotherapeutic agents[20-22] or short term culture with loss of viability as determined by staining due to loss of membrane integrity[23,24] or reduction of the tetrazolium salt, MTT[25-27]. One recent report used a short term (4 day) culture of acute lymphocytic leukemia cells over a marrow stroma cell layer and determined viable leukemic cells by flow cytometry[12]. Another recent report used a 2 day culture of ANNL cells followed by bromodeoxyuridine labeling and flow cytometric analysis of cell cycle[28]. The present assay has advantages over the colony growth assays of chemosensitivity in that it requires less than two days to complete rather than a week or more. Furthermore, all cells are assayed with the present assay as opposed to only those that grow into colonies. An advantage of the present assay over the cell viability assays is that it measures apoptotic cells which still have intact plasma membranes and, thus, are not counted in the usual cell viability assay. Also, rather than the single, one-time reading of the viability assays, the present assay permits continuous readings of the same culture. Compared to the stroma layer-flow cytometry method the present assay has the advantages that no stroma layer needs to be established, the culture time is less, and flow cytometry is not required for the assay. The advantage of the present assay compared to the short term culture-cell cycle assay is that the present assay does not require bromodeoxyuridine labeling or flow cytometry. Despite each of these specific advantages of the present assay, its greatest potential is its simplicity.

Development of the Microculture Kinetic Assay for Apoptosis

Incubated scanning microplate readers such as the THERMOmax reader (Molecular Devices) or the MR 5000 reader (Dynatech) make possible the continuous monitoring of both suspension and adherence cultures of malignant cells[5]. The potential problems of medium evaporation, sterility, and pH were overcome by preincubating the microcultures in a humidified, $CO_2$-controlled atmosphere and then layering sterile mineral oil over each culture. With as few as $1.0 \times 10^5$ cells per 250 $\mu$liters, cultures can be accurately monitored for cell growth for 72 hours or longer by determining light absorbance[5].

Agents which caused apoptosis in lower concentrations and necrosis in higher concentrations were added to present assay of the leukemic cell line HL-60[6] and the curves that resulted from plotting O.D. versus time were evaluated (FIG. 1). Results for ethanol and hydrogen peroxide are shown in FIGS. 1a and 1b, respectively. At the lowest tested concentrations of either agent, the treated cultures showed a slight loss of O.D. in the first few hours followed by a period of more rapidly increasing O.D. for several hours and finally a slower rate of increasing O.D. Although only the first 15 hours are shown in FIGS. 1a and 1b, the O.D. curves for the all treated cultures became less than the control culture after 24 hours. When the doses of ethanol or $H_2O_2$ were increased, the "apoptosis" O.D. curves became more pronounced. More prominent decreases in O.D. in the first few hours were followed by very steep rises in O.D. that were in turn followed by plateaus or declines in the O.D. curves (FIGS. 1a and 1b). The ultimate decline in O.D. below control values occurred at earlier times as the doses of ethanol or $H_2O_2$ were increased. By examining the cells at various times of culture for morphological evidence of apoptosis, it was found that the maximum apoptosis occurred after the rapidly rising component of the O.D. curve, when the O.D. values reached a plateau or began to decline slightly. In the assays shown in FIGS. 1a and 1b, the maximum apoptosis occurred at 6 to 7 hours (FIG. 2). Most importantly, the calculated best fit slope of the rapidly rising O.D. component (shown as dashed lines in FIG. 1) that precedes the period of maximum apoptosis, correlated very well with both the percentage of apoptotic cells (FIG. 2) and the degree of internucleosomal cleavage (FIG. 3) at 7 hours. When live HL-60 cells were examined for morphological evidence of apoptosis under Nomarski optics (FIG. 4a shows the morphological appearance of HL-60 cells under various conditions), the various components of the typical "apoptotic" O.D. curve could be related to specific sequential morphological changes of apoptosis as described by Cohen[29]. These relationships are shown in FIG. 4b. The early decrease in O.D. corresponded to cell shrinkage; the rapid increase in O.D. corresponded to cell blebbing and nuclear condensation; the subsequent plateau and/or decline in O.D. that follows the rapid increase in O.D. corresponded to lysis and fragmentation of cells (FIG. 4b). When 10% ethanol or 1 mM $H_2O_2$ were used in the cultures, internucleosomal cleavage of DNA was not seen (FIG. 3) and the O.D. versus time curves show a steady decline in O.D. without the rapidly increasing phase that characterized cells undergoing apoptosis (FIGS. 1a and 1b). After 1 h, more than 90% of the cells stained with trypan blue and had indistinct vacuolated cytoplasm consistent with necrosis.

Other curves of O.D. vs. time were also made from HL-60 cells treated with the chemotherapeutic agent cis-platinum (FIG. 5). In this case the same characteristic "apoptosis" curves of O.D. were found at all cis-platinum concentrations tested (FIG. 5) although the effect was slight at 10 $\mu$M. The time course for the apoptosis is more prolonged with cis-platinum than when either ethanol or $H_2O_2$ was used (FIGS. 1a and 1b). As in the case of ethanol and $H_2O_2$, however, the regression analysis of the slope of rapidly rising O.D. component of the apoptosis curve correlated very well with the percentages of apoptotic cells and DNA cleavage (FIG.

6). These results of ethanol, $H_2O_2$, etoposide and cis-platinum effects in the present assay along with other experiments show that the present assays were extremely reproducible and that cell clumping or cell enlargement did not give O.D. curves like those seen with apopotosis[6].

Assays of Leukemic Patient Samples

To demonstrate that the "apoptosis" O.D. curves found with cell lines also occurs in freshly isolated cells, chronic lymphocytic leukemia (CLL) cells were purified from the peripheral blood of four patients and tested in the present assay (FIGS. 7 & 8). In FIG. 7, patient #1 had recently diagnosed CLL that was clinically sensitive to corticosteroids, while patient #2 had extensive therapy that included corticosteroids and he had developed clinical evidence of corticosteroid-resistant CLL. In the present assay of purified CLL cells from the blood of patient #1 with the corticosteroid-sensitive disease, an apoptotic O.D. curve was seen with $10^{-6}$ M dexamethasone (FIG. 7). With CLL cells from patient #2 with corticosteroid-resistant disease, no effects of dexamethasone were found at concentrations that were 100 times higher ($10^{-4}$ M dexamethasone) (FIG. 7). In FIG. 8, two other patients with CLL had their purified leukemic cells assayed with vincristine in the present assay. Patient #3 had a more vincristine-resistant CLL as shown by the similarity of his apoptosis O.D. curve at 10 µg/ml vincristine and the apoptosis O.D. curve of the CLL cells from patient #4 at 100 times less (0.1 µg/ml) vincristine (FIG. 8). FIGS. 7 and 8 also demonstrate two other characteristics of the present assay when CLL cells are cultured with chemotherapeutic agents. First, unlike HL-60 cells which grow spontaneously, the untreated control CLL cells survive in culture but do not proliferate. This survival without growth is represented by the relatively flat or slightly declining curves for control cultures in FIGS. 7 and 8 over time as compared to the increasing O.D. control curves of HL-60 cells (FIGS. 1 and 5) over the same time course. Second, when compared to ethanol and $H_2O_2$, the time courses were more protracted with standard chemotherapeutic agents. With dexamethasone and vincristine, the peak of apoptosis occurs at about 24 hours, while with cis-platinum the peak of apoptosis was at 52 hours. The O.D. curves, as expected, show time courses consistent with these peaks of apoptosis. The rapidly increasing phase of the apoptotic O.D. curve preceded the respective peak of morphologically recognized apoptosis by several hours (FIGS. 6, 7 and 8). The time course of the apoptosis depends upon several variables such as cellular uptake and retention of the agent or the phase of the cell cycle when the agent has a cell cycle-specific effect.

In FIGS. 9 and 10, assays according to the invention were performed with leukemic cells isolated from the blood of two newly diagnosed patients with acute non-lymphocytic leukemia (ANLL). In FIG. 9, the patient had an FAB class M1 leukemia. Clinically, the patient was resistant to chemotherapy and died within five weeks of diagnosis without achieving remission. In FIG. 10, the patient had an EAB class M2 leukemia. Clinically, the patient responded to induction chemotherapy and is now in a complete remission. The tracings from the assays for each dose of etoposide are shown in the "a" part of each figure. Untreated, control ANLL cells from both patients had factor-independent growth, as shown by a rising O.D. with time, just as did HL-60 cells-shown in FIGS. 1 and 5. In the "a" part of FIG. 10, R-values are the correlation coefficients of the best fit slopes for either the untreated, control cultures or the rapidly rising apoptotic component of the etoposide-treated cultures. B-values are the slopes of the control or etoposide curves. In FIGS. 9 and 10, the "b" parts show the calculated slopes ($B_R$) of the rapidly rising components of the apoptotic O.D. curves induced by etoposide in the ANLL cells. These $B_R$ slopes were calculated by subtracting the control slope from the corresponding etoposide slope (i.e., $B_{Etopo} - B_{control} = B_R$) shown in the experimental tracings in the part "a" of the FIGS. 9 and 10. This $B_R$ slope is used in the Methods section below to determine significance of response. In FIG. 9, the slopes of the control and etoposide curves were very similar; calculated slopes ($B_R$) in part "b" of FIG. 9 were either zero or slightly negative and they are shown as flat lines.

Clinical Significance of the Assay

The present results have direct and immediate clinical significance. Chemotherapy or radiation therapy kills cells by inducing apoptosis. Currently used chemosensitivity assays do not measure the apoptosis process directly but rather use end points based upon the death or survival of treated cells. When leukemic cells are exposed to a chemotherapeutic agentin vitro, the percentage of apoptotic cells in the population can be determined at a specific time by microscopic examination. However, while apoptotic cells exist much longer in vitro than they do in vivo, where they are promptly phagocytosed, they do disintegrate in vitro as shown in FIG. 4b. Thus, an accurate determination of apoptosis in a population of cells requires either frequent determinations or continuous monitoring. The present assay is an automated procedure that continuously measures the apoptosis process directly and thereby can more accurately detect the effects of chemotherapeutic agents on a specific tumor cell population.

From the information provided by the present assay, an accurate prediction of the response of an individual patient to chemotherapy and the probability of future relapse should a remission be induced can be made. When a relapse occurs, the present assay of the leukemic cells at that time should help identify any resistance that may have developed to a specific chemotherapeutic agent. If resistance is identified, the assay also has the potential to identify the sensitivities of the leukemic cells to alternative chemotherapeutic agents. In this manner, the present assay can be a guide to a more effective therapy in the patient with relapsed acute leukemia. The rapidity of the assay has the potential to permit adjustments in the dosage or even in the choice of chemotherapeutic agents to be used in the patient's treatment. The present results should also provide important information for longer term aims of identifying and altering the mechanisms of chemotherapy resistance that develop in relapsed leukemia.

Methods

Cell Procurement

Prior to any chemotherapy, a sample of venous blood (e.g., 1–30 ml) or a sample of bone marrow (e.g., 2–20 m: is obtained by direct needle aspiration under sterile conditions. The samples are drawn into a heparinized syringe and diluted with RPMI-1640 medium that contains phenol red. The mononuclear fraction of each sample is isolated by centrifugation using Ficoll-Hypaque. If erythrocytes contaminate the mononuclear cell fraction, then they are removed by treatment with red cell lysis buffer. After washing three times in phosphate buffered saline, an aliquot of the mononuclear cells is analyzed by either light microscopy or flow cytometry for purity and viability. The specific MAb's that recognized the leukemia cells in the diagnostic testing are used to check purity while 7-amino-actinomycin D (7AAD) is used to check viability. If purity and viability are both greater than 90%, then the cells are aliquoted for the present assays and for cryopreservation in RPMI-1640 containing 20% feta. bovine serum and 10% dimethylsulfoxide. Greater than 90% purity and viability would be expected in most cases with a high leukemic cell count in either the blood or bone marrow. If the mononuclear cell fraction purity is less than 90%, then the cells are further purified. T-lymphocytes and monocytes are removed by negative selection using immunomagnetic separation. MAb's to CD2 for T-cell removal and CD14 for monocyte removal and Dynabeads (Dynal, Inc.) are used in those cases in which the diagnostic immunophenotyping shows that the leukemic cells lack these surface antigens. After these immunomagnetic separations, the leukemic cell population will again be tested for purity.

Assay for Chemosensitivity

Purified leukemic cells are resuspended at from $1.0 \times 10^5$ to $4.0 \times 10^5$ cells/ml in RPMI-1640 medium without phenol red and with 10% fetal calf serum. Note that depending on the microwell plate and the O.D. reader, the concentration of cells may be significantly lower. Aliquots of 250 µliters are cultured in individual wells of a 96-well, flat-bottomed tissue culture microplate. Various concentrations of chemotherapeutic agents used to treat acute leukemias are added to duplicate cultures immediately prior to incubation at about 37° C. in 5% $CO_2$ in humidified air. The ranges of concentrations of the agents are based on a) previous reports of apoptosis induced in vitro by these specific agents in either fresh human leukemia cells or human leukemia cell lines and b) pharmacokinetic studies demonstrating that these ranges include concentrations of the parent drugs and/or their active metabolites found in patients following treatment for leukemia. In the present example, the leukemia samples from adults are tested with four agents that are used in their induction and consolidation therapy: 0.1–10.0 µM idarubicin[10,31]; 0.01–1.0 µM daunorubicin[11,31]; 0.01–10.0 µM cytosine arabinoside[12,13,32]; 0.1–10.0 µg etoposide[11,17,33] and 0.01–1 µM mitoxantrone[16,34,35]. For leukemia samples from children, the same concentrations of cytosine arabinoside and etoposide as listed above for adult samples are examined. In place of idarubicin in the adults, daunorubicin at concentrations of 0.01–1 µM are tested. Control wells will receive an equal volume of solvent used for each chemotherapeutic agent. After 30 minutes incubation in humidified air plus 5% $CO_2$, 60 µliters of sterile light mineral oil is layered over each culture, the microplate covered with a lid, and placed in the incubated microplate reader. The O.D. at 600 nm (590–650 nm) of each culture is monitored every five minutes over the ensuing 48 hour period. The cultures are shaken with the mixing mode of the incubated microplate reader before each reading is made.

Sample Size and Statistical Power Analysis

The present method is able to predict more accurately at the time of initial diagnosis which patients will have a relapse by using the present assay of apoptosis to assess the chemosensitivity of acute leukemias. To establish this, the accumulated O.D. data for each culture are analyzed and displayed using a kinetics software program provided with the incubated microplate reader. Except for Ara-C, all of the chemotherapeutic agents are tested at five concentrations covering a 100-fold range. For example, idaurubicin is tested at 0.1, 0.3, 1, 3, and 10 µM. Ara-C is tested at seven concentrations covering a 1,000-fold range—0.01, 0.03, 0.1, 0.3, 1, 3, and 10 µM.

Figure 11:
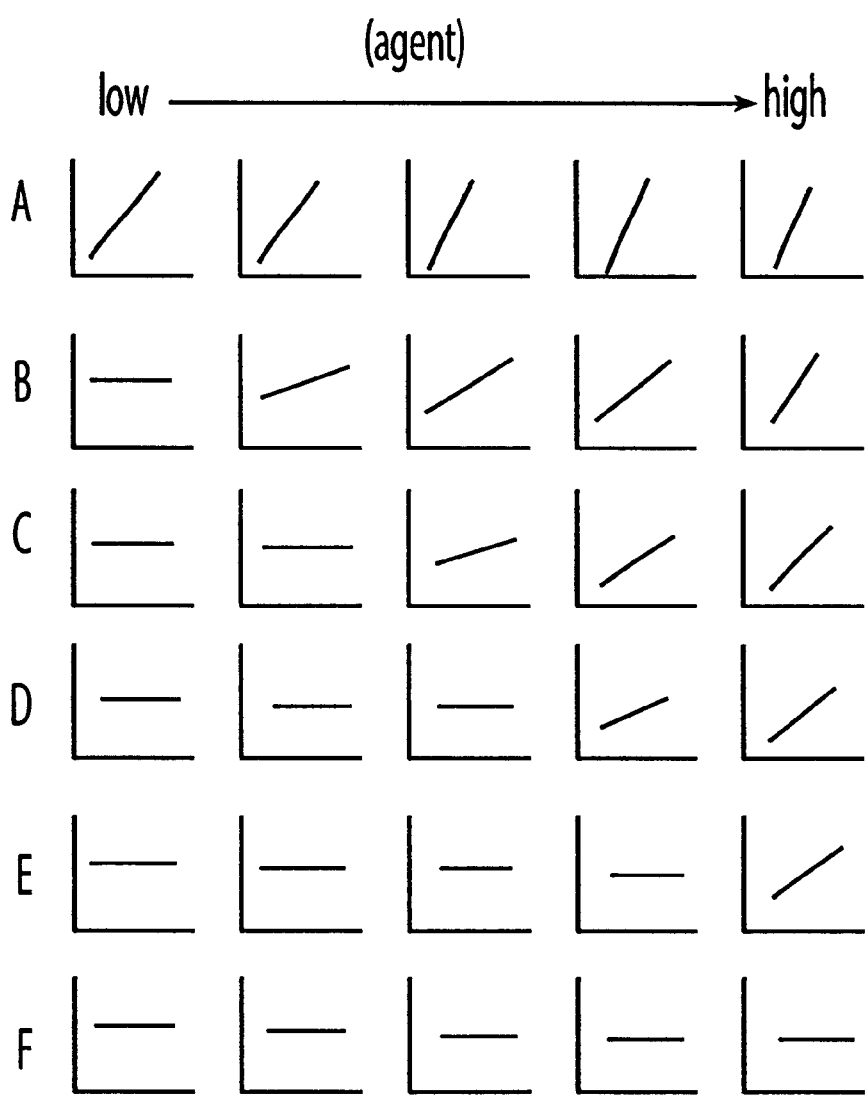

A series of curves plotting O.D. versus time of culture are made from the results obtained at the different concentrations of each agent, similar to the curves shown in FIGS. 1a, 1b, 5, 7–10. We expect to have a range of chemosensitivities with the present assay as demonstrated in FIG. 11. This figure shows the expected patterns of slopes of O.D. vs. time for a single agent. These slopes are calculated as the $B_R$ slopes in FIG. 9 and 10. In this figure, fresh leukemia cells when cultured without any agent would be expected to give a steadily rising O.D. vs. time curve as did the fresh leukemic cells in control curves in FIGS. 9a and 10a. Likewise, a concentration of an agent which has no effect on the leukemic cells will also give the same rising curve as the untreated cells as occurred with the patient's cells shown in FIG. 9. Any concentration of an agent inducing apoptosis gives a sharply rising slope O.D. vs. time as occurred in FIG. 10. In FIG. 11, a range of responses of leukemias is shown for five doses covering a 100-fold difference from low dose in those panels on the extreme left to high dose on the extreme right panels. Patterns A through F vary from the extremely sensitive leukemic cells in pattern A in which every concentration of the agent induced apoptosis to pattern F in which no effect of the agent is found at any concentration including the highest used. The present results predict that patients with patterns A and B, are most likely to have remissions without relapse. The patient shown in FIG. 10 had a B pattern; patients with patterns C, D, and E would achieve remission, but would be very likely to have a subsequent relapse. Patients with pattern F, like the patient in FIG. 9, would be most likely to fail to achieve remission. The criterion for classifying the present assay results is given as follows: a patient's leukemia is considered predictive of a relapse, if the rapid rising component of the O.D. curves occurs only above the 40th percentile of the range of concentrations for one or two chemotherapeutic agents (i.e., patients with patterns C, D, or E).

Statistical Analysis

Demographic information such as age, race, and gender are tabulated. Descriptive statistics, including means, standard deviations, and ranges for continuous parameters, as well as percents and frequencies for categorical parameters, are presented overall and for adult or pediatric patients as separate groups. Student t-test is used to compare continuous parameters; Chi-square or Fisher's exact test is used as appropriate to compare categorical parameters at initial diagnosis[40].

The exact two-sided 95% confidence limits and sensitivity analysis for the accuracy of the prediction of which patients will have a relapse by using the present microculture kinetic assay are determined. Student t-test or Fisher's exact test is used as appropriate to address the association of the present assay results and other prognostic factors such as leukemic cell numbers in the blood at diagnosis, age of the patient[41] preceding myelodysplastic syndrome[42], cytogenetics abnormalities[1], FAB classification[43] and immunophenotyping[44].

When any patient whose leukemia was previously assayed at the time of diagnosis has a relapse, another blood or marrow sample is obtained. The leukemic cells are purified and the present assays repeated with the same concentrations of chemotherapeutic agents that were used in the assays at the time of initial diagnosis. Aliquots of purified leukemic cells at relapse are cryopreserved by the same procedures described for the samples obtained at initial diagnosis. To confirm the present assay results indicating that resistance to a specific agent has developed in a patient with relapsed leukemia, cryopreserved aliquots of the patient's initial diagnosis sample and relapse sample are thawed and compared directly in the present assay and by fluorescence-Tdt analysis. At the same concentration of the agent, decreased apoptosis would be expected to be found in both analyses with the relapse sample as compared to the initial diagnosis sample. Test of hypotheses concerning the ability of the present assay of apoptosis to identify the resistance to specific chemotherapeutic agents in relapsed acute leukemias is completed using paired t-test or McNemar's test to determine the differences in the slopes of the rapidly rising component of the O.D. curves.

Clinical Application

Since, the present assay is an accurate predictor of response to chemotherapy in ANLL, then direct application of the assay to the care of patients with leukemia can be made immediately. We have shown that the present assay can detect clinical resistance to chemotherapeutic agents in both ANLL (FIGS. 9 and 10) and CLL (FIGS. 7 and 8). However, any malignancy which can be made into a single cell suspension could be tested in the present assay.

The present assay is especially valuable in the care of patients whose leukemia has relapsed. If resistance of a patient's leukemia to a chemotherapeutic agent is demonstrated with the present assay, then further studies with the present assay can be performed to help in determining the reinduction therapy, i.e., which drugs at which doses. Alternative drugs to the one against which resistance has developed can be tested in the present assay with the patients leukemic cells. Also, the sensitivity of the leukemia can be tested against combinations of the two or more chemotherapeutic agents. Finally, modulators of chemosensitivity can be tested directly with the chemotherapeutic agents in the present assay. For example, cyclosporine A or verapamil, which increase the daunorubicin accumulation and retention in ANLL cells with increased md-1 expression[61,62] can be tested at various doses with leukemic cells exposed to at daunorubicin in the present assay. Another example is the possibility to test directly all trans-retinoic acid or G-CSF in combination with Ara-C in the present assay. These two hematopoietic agents have been shown to sensitize ANLL cells to Ara-C[63,64]. The major advantages of the present assay for these studies are that up to 96 aliquots from one blood sample can be tested simultaneously and in an automated manner within a period of 2 days. The results from these tests can then guide the reinduction therapy for the specific patient with relapsed leukemia that is being treated.

REFERENCES

1. Rowley J D: Recurring chromosome abnormalities in leukemia and lymphoma. Semin Hematol 27:122, 1990
2. Hunter A E, Rogers S Y, Roberts I A G, Barrett A J, Russell N: Autonomous growth of blast cells is associated with reduced survival in acute myeloblastic leukemia. Blood 82:899, 1993
3. Lowenberg B, Van Putten W, Touw I, Delwel R, Santini V: Autonomous proliferation of leukemic cells in vitro as a determinant of prognosis in adult acute myeloid leukemia. N Engl J Med 328:614, 1993
4. Veerman A J P, Pieters R: Drug sensitivity assays in leukaemia and lymphoma. Br J Haematol 74:381, 1990
5. Kravtsov V: A novel microculture kinetic assay (MiCK Assay) for malignant cell growth and chemosensitivity. Eur J Cancer 30:1564, 1994
6. Kravtsov V, Fabian I: Automated monitoring of apoptosis in suspension cell cultures. Lab Invest 74:557, 1996
7. Wyllie A H, Kerr J F R, Currie A R: Cell death: The significance of apoptosis. Int Rev Cytol 68:251, 1998
8. Arends M J, Wyllie A H: Apoptosis: Mechanisms and roles in pathology. Int Rev Exp Pathol 32:223, 1991
9. Gunji H, Kharbanda S, Kufe D: Induction of internucleosomal DNA fragmentation in human myeloid leukemia cells by 1-beta-D-arabinofuranosylcytosine. Cancer Res 51:741, 1991
10. Zwelling L A, Bales E, Altschuler E, Mayes J: Circumvention of resistance by doxorubicin, but not by idarubicin, in a human leukemia cell line containing an intercalator-resistant form of topoisomerase II. Biochem Pharmacol 45:516, 1993
11. Karp J E, Jones R J, Miller C B, Schneider E, Zwelling L A, Cowan K, Wendel K, Burke P J:
Topoisomerase II levels and drug sensitivity in adult acute myelogenous leukemia. Blood 83:517, 1994
12. Campana D, Manabe A, Evans W E: Stroma-supported immunocytometric assay (SIA): a novel method for testing the sensitivity of acute lymphoblastic leukemia cells to cytotoxic drugs. Leukemia 7:482, 1993
13. Bhalla K, Tang C, Ibrado A M, Grant S, Tourkina E, Holladay C, Hughes M, Mahoney M E, Huang Y: Granulocyte-macrophage colony-stimulating factor/interleukin-3 fusion protein (pIXY 321) Enhances high-dose Ara-C-induced programmed cell death or apoptosis in human myeloid leukemia cells. Blood 80:2883, 1992
14. Miyashita T, Reed J C: Bcl-2 oncoprotein blocks chemotherapy-induced apoptosis in a human leukemia cell line. Blood 81:151, 1993
15. Lotem J, Sachs L: Hematopoietic cytokines inhibit apoptosis induced by transforming growth factor beta-1 and cancer chemotherapy compounds Blood 80:1750, 1992
16. Bhalla K, Ibrado A M, Tourkina E, Tang C, Grant S, Bullock G, Huang Y, Ponnathpur V, Mahoney M E: High-dose mitoxantrone induces programmed cell death or apoptosis in human myeloid leukemia cells. Blood 82:3133, 1993
17. Chiron M, Demur C, Pierson V, Jaffrezou J-P, Muller C, Saivin S, Bordier C, Bousquet C, Dastugue N, Laurent G: Sensitivity of fresh acute myeloid leukemia cells to etoposide: Relationship with cell growth characteristics and DNA single-strand breaks. Blood 80:1307, 1992
18. Li X, Gong J, Feldman E, Seiter K, Traganos F, Darzynkiewicz Z: Leukemia Lymphoma 13:65, 1994
19. Gorczyca W, Bruno S, Darzynkiewicz R J, Gong J, Darzynkiewicz Z: DNA strand breaks occurring during apoptosis: Their early in situ detection by the terminal deoxynucleotidyl transferase and nick translation assays and prevention by serine protease inhibitors. Int j Oncol 1:639, 1992
20. Park C H, Wiernik P H, Morrison F S, Amare M, vanSloten K, Maloney T R: Clinical correlations of leukemic clonogenic cell chemosensitivity assessed by in vitro continuous exposure to drugs. Cancer Res 43:2346, 1983
21. Preisler H D: Prediction of response to chemotherapy in acute meyelocytic leukemia. Blood 56:361, 1980
22. Park C H, Amare M, Savin M A, Goodwin J W, Newcomb M M, Hoogstraten P: Prediction of chemotherapy response in human leukemia using an in vitro chemotherapy sensitivity test on the leukemic colony-forming cells. Blood 55:595, 1980
23. Weisenthal L M, Dill P L, Finklestein J Z, Duarte T E, Baker J A, Moran E M: Laboratory detection of primary and acquired drug resistance in human lymphatic neoplasms. Cancer Treatment Reports 70:1283, 1986

24. Tidefelt U, Sundman-Engberg B, Paul C: Effects of verapamil on uptake and in vitro toxicity of anthracyclines in human leukemic blast cells. Eur J Haematol 40:385, 1988

25. Pieters R, Huismans D R, Leyva A, Veerman A J P: Comparison of a rapid automated tetrazolium based (MTT)-assay with a dye exclusion assay for chemosensitivity testing in childhood leukaemia. Br J Cancer 59:217, 1989

26. Sargent J M, Taylor C G: Appraisal of the MITT assay as a rapid test of chemosensitivity in acute myeloid leukaemia. Br J Cancer 60:206, 1989

27. Twentyman P R, Fox N E, Rees J K H: Chemosensitivity testing of fresh leukaemia cells using the MTT colorimetric assay. Br J Haematol 71:19, 1989

28. Lacombe F, Belloc F, Dumain P, Puntous M, Cony Makhoul P, Saux M-C, Bernard P, Boisseau M R, Reiffers J: Detection of cytarabine resistance in patients with acute myelogenous leukemia using flow cytometry. Blood 84:716, 1994

29. Cohen J J: Overview: Mechanisms of apoptosis. Immunol Today 14:126, 1993

30. Larson R S, McCurley T L: CD4 predicts nonlymphocytic lineage in acute leukemia: Insights from analysis of 125 cases using two color flow cytometry. Am J Clin Path in press:1995

31. Tidefelt U, Sundman-Engberg B, Paul C: Comparison of the intracellular pharmacokinetics of daunorubicin and idarubicin in patients with acute leukemia. Leuk Res 18:293, 1994

32. Chabner B: Cytidine Analogues, in Chabner B A, Collins J M (eds): Cancer Chemotherapy Principles and Practice, Philadelphia, J.B. Lippincott Co., 1990, p 154

33. Hande K R, Wedlund P J, Noone R N, Wilkinson G R, Greco F A, Wolff S N: Pharmacokinetics of high-dose etoposide (VP-16-213) administered to cancer patients. Cancer Res 44:379, 1984

34. Alberts D S, Peng Y M, Leigh S, Davis T P, Woodward D L: Disposition of mitoxantrone in cancer patients. Cancer Res 45:1879, 1985

35. Smyth J F, Macpherson J S, Warrington P S, Leonard R C F, Wolf C R: The clinical pharmacology of mitoxantrone. Cancer Chemother Parmacol 17:149, 1986

36. Brox L W, Birkett L, Belch A: Clinical pharmacology of oral thioguanine in acute myelogenous leukemia. Cancer Chemother Parmacol 6:35, 1981

37. Morgan C J, Chawdry R N, Smith A R, Siravo-Sagraves G, Trewyn R W: 6-Thioguanine-induced growth arrest in 6-mercaptopurine-resistant human leukemia cells. Cancer Res 54:5387, 1994

38. Kelley L, Green W, Hicks G, Bondurant M, Koury M, Ruley H: Apoptosis in erythroid progenitors deprived of erythropoietin occurs during G1 and S phases of the cell cycle without growth arrest or stabilization of wild-type p53. Mol Cell Biol 14:4183, 1994

39. Hintze Jerry L: Power Analysis and Sample Size (software—Version 1.0). Kaysville, Utah, NCSS/PASS, 1991

40. Woolson Robert F: Statistical Methods for the Analysis of Biomedical Data. New York, John Wiley & Sons, 1987

41. Brincker H: Estimate of overall treatment results in acute nonlymphocytic leukemia based on age-specific rates of incidence and of complete remission. Cancer Treat Rep 69:5, 1985

42. Hoyle C F, et al: AML associated with previous cytotoxic therapy, MDS or myeloproliferative disorders: Results from the MRC's 9th AML trial. Br J Haematol 72:45, 1989

43. Peterson B A, Levine E G: Uncommon subtypes of acute non-lymphocytic leukemia: clinical features and management of FAB M5, M6, and M7. Semin Oncol 14:425, 1987

44. Bradstock K, Matthews J, Benson E, Page F, Bishop J: Prognostic value of immunophenotyping in acute myeloid leukemia. Blood 84:1220, 1994

45. Pirker R, Wallner J, Geissler K, Linkesch W, Haas O A, Bettelheim P, Hopfner M, Scherrer R, Valent P, Havelec L, Ludwig H, Lechner K: MDR1 gene expression and treatment outcome in acute myeloid leukemia. J Natl Cancer Inst 83:708, 1991

46. Goasguen J E, Dossot J-M, Fardel O, Le Mee F, Le Gall E, Leblay R, LePrise P Y, Chaperon J, Fauchet R: Expression of the multidrug resistance-associated P-glycoprotein (P-170 in 59 cases of de novo acute lymphoblastic leukemia prognostic implications. Blood 81:2394, 1993

47. Schneider E, Cowan K H, Bader H, Toomey S, Schwartz G N, Karp J E, Burke P J, Kaufmann S H: Increased expression of the multidrug resistance-associated protein gene in relapsed acute leukemia. Blood 85:186, 1995

48. Lippman M E, Yarbro G K, Leventhal B G: Clinical implications of glucocorticoid receptors in human leukemia. Cancer Res 38:4251, 1978

49. Quddus F F, Leventhal B G, Boyett J M, Pullen D J, Crist W M, Borowitz M J: Glucocorticoid receptors in immunological subtypes of childhood acute lymphocytic leukemia cells. Cancer Res 45:6482, 1985

50. Costlow M E, Pui C H, Dahl G V: Glucocorticoid receptors in childhood acute lymphocytic leukemia. Cancer Res 42:4801, 1982

51. Campos L, Rouault J P, Sabido O, Oriol P, Roubi N, Vasselon C, Archimbaud E, Magaud J P, Guyotat D: High expression of bcl-2 protein in acute myeloid leukemia cells is associated with poor response to chemotherapy. Blood 81:3091, 1993

52. Compana D, Coustan-Smith E, Manabe A, Buschle M, Raimondi S C, Behm F G, Ashmun R, Arico M, Biondi A, Pui C-H: Prolonged survival of B-lineage. acute lymphoblastic leukemia cells is accompanied by overexpression of bcl-2 protein. Blood 81:1025, 1993

53. Kozopas K M, Yang T, Buchan H L, Zhou P, Craig C W: MCL1, a gene expressed in programmed myeloid cell differentiation, has sequence similarity to bcl-2. Proc Natl Acad Sci USA 90:3516, 1993

54. Felix C A, Nau M M, Takasashi T, Mitsudomi T, Chiba I, Poplak D G, Reaman G H, Cole D E, Letterio J J, Whang-Peng J, Knutsen T, Minna J D: Hereditary and acquired p53 gene mutations in childhood acute lymphopablstic leukemia. J Clin Invest 89:640, 1992

55. Lotem J, Sachs L: Regulation by bcl-2, c-myc and p53 of susceptability to induction of apoptosis by heat shock and cancer chemotherapy compounds in differentiation competent and defective myeloid leukemic cells. Cell Growth and Diff 4:41, 1993

56. Zhang W, Hu G, Estey E, Hester J, Deisseroth A: Altered conformation of the p53 protein in myeloid leukemia cells and mitogen-stimiulated normal blood cells. Oncogene 7:1645, 1992
57. Zhu Y M, Bradbury D, Russell N: Expression of different conformations of p53 in the blast cells of acute myeloblastic leukaemia is related to in vitro growth characteristics. Br J Cancer 68:851, 1993
58. Sugimoto K, Toyoshima H, Sakai R, Miyagawa K, Hagiwara K, Hirai H, Ishikawa F, Takakau F: Mutations of the p53 gene in lymphoid leukemia. Blood 77:1153, 1991
59. Gaidano G, Ballerini P, Gong J Z, Inghirami G, Neri A, Newcomb E W, Magrath I T, Knowles D M, Dalla-Favera R: p53 mutations in human lymphoid malignancies: Association with Burkitt's lymphoma and chronic lymphocytic leukemia. Proc Natl Acad Sci USA 88:5413, 1991
60. Sugimoto K, Hirano N, Toyoshima H, Chiba S, Mano H, Takaku F, Yazaki Y, Hirai H: Mutations of the p53 gene in myelodysplastic syndrome (MDS) and MDS-derived leukemia. Blood 81:3022, 1993
61. Ross D D, Wooten P J, Sridhara R, Ordonez J V, Lee E J: Enhancement of daunorubicin accumulation, retention, and cytotoxicity by verapamil or cyclosporin A in blast cells from patients with previously untreated acute myeloid leukemia. Blood 82:1288, 1993
62. List A F, Spier C, Greer J, Wolff S, Hutter J, Dorr R, Salmon S, Futscher B, Baier M, Dalton W: Phase I/II trial of cyclosporine as a chemotherapy-resistance modifier in acute leukemia. J Clin Oncol 11:1652, 1993
63. Miyauchi J, Kellerher C A, Wang C, Minkin S, McCulloch E A: Growth factors influence the sensitivity of leukemic stem cells to cytosine arabinoside in culture. Blood 73:1272, 1989
64. Yang G S, Minden M D, McCulloch E A: Regulation by retinoic acid and hydrocortisone of the anthracycline sensitivity of blast cells of acute myeloblastic leukemia. Leukemia 8:2065,
65. Koury M J, Bondurant M C: Erythropoietin retards DNA breakdown and prevents programmed death in erythroid progenitor cells. Science 248:378, 1990
66. Williams G T, Smith C A, Spooncer E, Dexter T M, Taylor D R: Haemopoietic colony stimulating factors promote cell survival by suppressing apoptosis. Nature 343:76, 1990
67. Koury M J, Horne D W: Apoptosis mediates and thymidine prevents erythroblast destruction in folate deficiency anemia. Proc Natl Acad Sci USA 91:4067, 1993
68. Kravtsov V, Lasunskaya E, Freidlin I: The effects of mononuclear phagocytes on differentiation of syngeneic, allogeneic, allogeneic and xenogeneic haemopoietic stem cells. Tsitologia 29:1156, 1987
69. Kravtsov V, Lasunskaya E, Freidlin I: The interaction of macrophages and haemopoietic stem cells in vitro and in vivo. Tsitologia 31:359, 1989
70. Fabian I, Kravtsov V, Elis A, Gurevitch O, Ackerstein A, Slavin S, Nagler A: Eosinophils activation in post autologous bone marrow transplanted patients treated with subcutaneous interleukin-2 and interferon-alpha 2A immunotherapy. Leukemia 8:1379, 1994

What is claimed is:

1. A method of determining the apoptosis-inducing activity of a substance, which comprises:
    a) measuring the optical density of a first cell culture at more than one time point, wherein the first cell culture was contacted with the substance;
    b) measuring the optical density of a second cell culture at more than one time point, wherein the second cell culture was not contacted with the substance; and
    c) determining a net slope, which is the difference between the optical density change over time of the first cell culture and the optical density change over time of the second cell culture;

wherein a positive net slope indicates apoptosis-inducing activity of the substance.

2. A method of determining resistance of cells to the apoptosis-inducing activity of a substance, comprising:
    a) measuring the optical density of a first cell culture at more than one time point, wherein the first cell culture was contacted with the substance;
    b) measuring the optical density of a second cell culture at more than one time point, wherein the second cell culture was contacted with the substance and is apoptotically sensitive to the substance; and
    c) determining a net slope, which is the difference between the optical density change over time of the first cell culture and the optical density change over time of the second cell culture;

wherein a positive net slope indicates resistance of the first cell culture to the apoptosis-inducing activity of the substance.

3. The method of claim 1 or 2, wherein the net slope is determined by a method which comprises subtracting at each time point the optical density measurement of the second cell culture from the corresponding optical density measurement of the first cell culture.

4. The method of claim 1 or 2, wherein the net slope is determined by a method which comprises:
    calculating the rate at which the optical density of the first cell culture changes over time to provide a first rate of change;
    calculating the rate at which the optical density of the second cell culture changes over time to provide a second rate of change; and
    subtracting the second rate of change from the first rate of change.

5. The method of claim 1 or 2 wherein the cells are cultured at a concentration of at least $1.0 \times 10^4$ cells per 250 microliters.

6. The method of claim 1 or 2 wherein the optical density of the culture is measured from 590 to 650 nanometers.

7. The method of claim 1 or 2 wherein the substance is idarubicin, mitoxantrone, daunorubicin, etoposide, cytosine arabinoside, vinblastine, vincristine, doxorubicin, fludarabine, cisplatinum, cladribine, or dexamethasone.

8. The method of claim 1 or 2 which further comprises exposing the first cell culture to an agent that affects the intracellular concentration of the substance.

9. The method of claim 8 wherein the agent is cyclosporine A or verapamil.

* * * * *